US008637479B2

(12) United States Patent
Bandholtz et al.

(10) Patent No.: US 8,637,479 B2
(45) Date of Patent: Jan. 28, 2014

(54) COMPOUNDS AND METHODS FOR THE TREATMENT OF INFLAMMATORY DISEASES OF THE CNS

(75) Inventors: Lisa C. Bandholtz, Stockholm (SE);
Alexander Gielen, Bandhagen (SE);
Arezou Zargari, Solna (SE); Oliver Von Stein, Upplands Väsby (SE);
Lars-Göran Axelsson, Tierp (SE)

(73) Assignee: Index Pharmaceuticals AB, Stockholm (SE)

( * ) Notice: Subject to any disclaimer, the term of this patent is extended or adjusted under 35 U.S.C. 154(b) by 0 days.

(21) Appl. No.: 13/127,190

(22) PCT Filed: Nov. 4, 2009

(86) PCT No.: PCT/SE2009/051247
§ 371 (c)(1),
(2), (4) Date: Jul. 25, 2011

(87) PCT Pub. No.: WO2010/053435
PCT Pub. Date: May 14, 2010

(65) Prior Publication Data
US 2011/0293702 A1 Dec. 1, 2011

Related U.S. Application Data

(60) Provisional application No. 61/111,287, filed on Nov. 4, 2008.

(51) Int. Cl.
*A61K 48/00* (2006.01)
*A61K 38/00* (2006.01)

(52) U.S. Cl.
USPC ....................................... 514/44 R; 514/17.9

(58) Field of Classification Search
None
See application file for complete search history.

(56) References Cited

U.S. PATENT DOCUMENTS

| 8,309,529 B2 * | 11/2012 | Karlsson et al. ............. 514/44 R |
| 2008/0045473 A1 | 2/2008 | Uhlmann et al. |
| 2009/0263405 A1 | 10/2009 | Verthelyi et al. |

FOREIGN PATENT DOCUMENTS

| WO | 2004/016805 A2 | 2/2004 |
| WO | 2006/063072 A2 | 6/2006 |
| WO | 2006/065751 A2 | 6/2006 |
| WO | WO 2006063072 A2 * | 6/2006 |
| WO | 2007/004977 A1 | 1/2007 |
| WO | 2007/004979 A1 | 1/2007 |
| WO | 2007/050034 A1 | 5/2007 |
| WO | 2007/095316 A2 | 8/2007 |
| WO | 2008/136748 A1 | 11/2007 |
| WO | 2008/147956 A2 | 12/2008 |
| WO | 2009/045145 A1 | 4/2009 |
| WO | 2009/154565 A1 | 12/2009 |

OTHER PUBLICATIONS

Patole et al, Current Medicinal Chemistry, 13:3061-3067 (2006). Govt. of the USA.
Aravalli et al, J. Neuroimmune. Phamracol., 2:297-312 (2007).
GSN Database Accession No. ATZ65416, XP-002689557 (Feb. 5, 2009).
Supplementary Search Report from corresponding European Application No. 09825063.2 dated Jan. 10, 2013.

* cited by examiner

*Primary Examiner* — Tracy Vivlemore
*Assistant Examiner* — Kate Poliakova-Georgan
(74) *Attorney, Agent, or Firm* — Porter Wright Morris & Arthur LLP

(57) ABSTRACT

Inflammatory diseases in the CNS can be treated or alleviated by the administration of an oligonucleotide in an amount sufficient to reduce the influx of mononuclear cells to the central nervous system by down-regulating the expression of at least one cell surface marker. For example multiple sclerosis can be treated or at least alleviated, by the administration of an oligonucleotide in a dose effective to inhibit or reduce the influx of mononuclear and/or autoaggressive cells to the central nervous system. The oligonucleotide can be used alone, or in combination with other treatment strategies.

25 Claims, 20 Drawing Sheets

US 8,637,479 B2

SEQUENCE LISTING

```
<160> NUMBER OF SEQ ID NOS: 10

<210> SEQ ID NO 1
<211> LENGTH: 13
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
```

```
<223> OTHER INFORMATION: phosphorothioate modification
<220> FEATURE:
<221> NAME/KEY: misc_feature
<222> LOCATION: (10)..(12)
<223> OTHER INFORMATION: phosphorothioate modification

<400> SEQUENCE: 1
gggtcgcagc tgg                                                        13

<210> SEQ ID NO 2
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (12)..(14)
<223> OTHER INFORMATION: phosphorothioate modification

<400> SEQUENCE: 2
ggggtcgtct gcggg                                                      15

<210> SEQ ID NO 3
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (18)..(20)
<223> OTHER INFORMATION: phosphorothioate modification

<400> SEQUENCE: 3
tcgtcgttcg gccgatcgtc c                                               21

<210> SEQ ID NO 4
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (12)..(14)
<223> OTHER INFORMATION: phosphorothioate modification

<400> SEQUENCE: 4
ggggtcgcag ctggg                                                      15

<210> SEQ ID NO 5
<211> LENGTH: 14
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
```

```
<223> OTHER INFORMATION: phosphorothioate modification
<220> FEATURE:
<221> NAME/KEY: misc_feature
<222> LOCATION: (11)..(13)
<223> OTHER INFORMATION: phosphorothioate modification

<400> SEQUENCE: 5
ggggtcgtct gcgg                                                         14

<210> SEQ ID NO 6
<211> LENGTH: 22
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (19)..(21)
<223> OTHER INFORMATION: phosphorothioate modification

<400> SEQUENCE: 6
tcgtcgttct gccatcgtcg tt                                                22

<210> SEQ ID NO 7
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (13)..(15)
<223> OTHER INFORMATION: phosphorothioate modification

<400> SEQUENCE: 7
gatcgtccgt cggggg                                                       16

<210> SEQ ID NO 8
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: phosphorothioate modification
<220> FEATURE:
<221> NAME/KEY: misc_feature
<222> LOCATION: (12)..(14)
<223> OTHER INFORMATION: phosphorothioate modification

<400> SEQUENCE: 8
ggggatcgtc cgggg                                                        15

<210> SEQ ID NO 9
<211> LENGTH: 19
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
```

```
<223> OTHER INFORMATION: phosphorothioate modification
<220> FEATURE:
<221> NAME/KEY: misc_feature
<222> LOCATION: (16)..(18)
<223> OTHER INFORMATION: phosphorothioate modification

<400> SEQUENCE: 9
ggaacagttc gtccatggc                                              19

<210> SEQ ID NO 10
<211> LENGTH: 20
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(2)
<223> OTHER INFORMATION: phosphorothioate modification
<220> FEATURE:
<221> NAME/KEY: misc_feature
<222> LOCATION: (15)..(19)
<223> OTHER INFORMATION: phosphorothioate modification

<400> SEQUENCE: 10
gggggacgat cgtcgggggg                                             20
```

COMPOUNDS AND METHODS FOR THE TREATMENT OF INFLAMMATORY DISEASES OF THE CNS

RELATED APPLICATIONS

Figure 1:
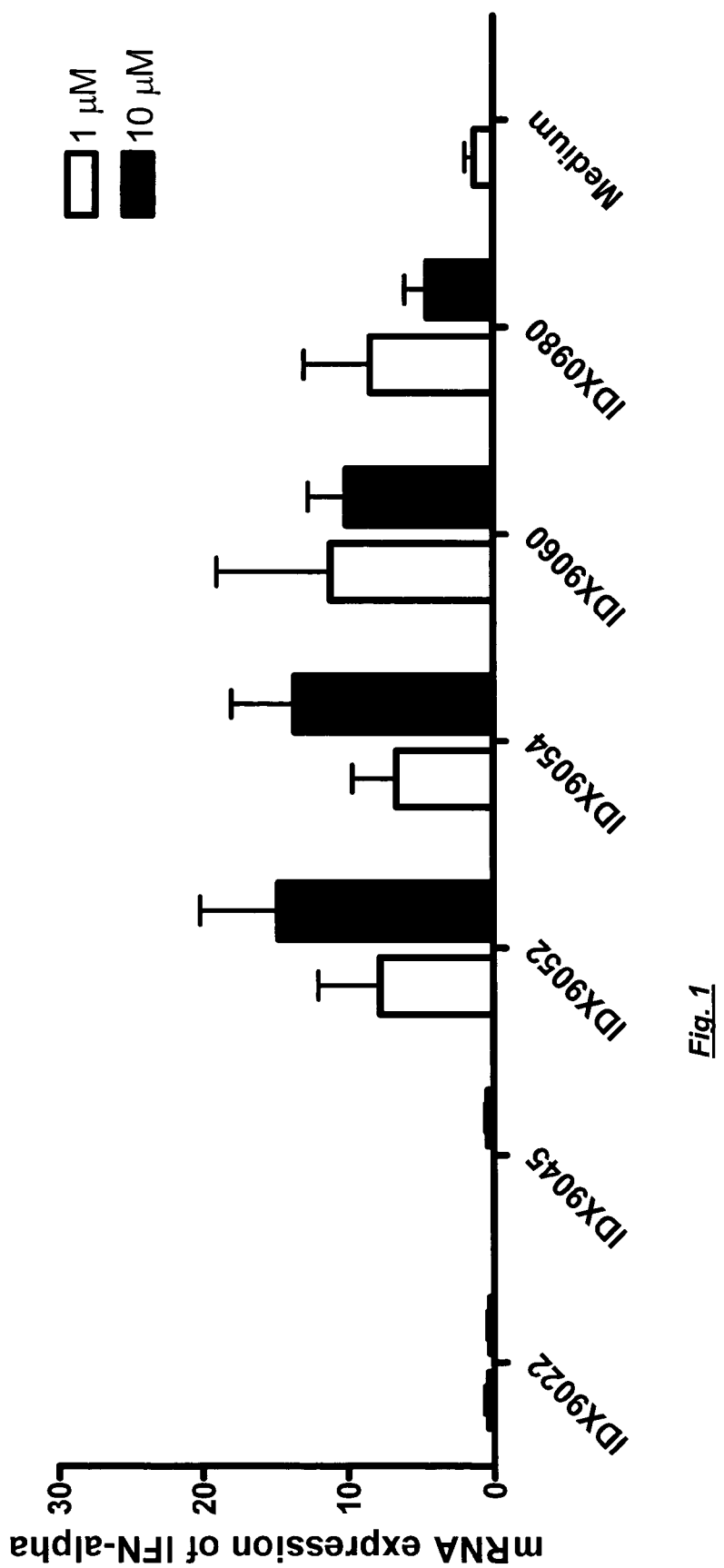

The present application is a 371 of PCT/SE2009/051247 filed Nov. 4, 2009 and claims priority under 35 U.S.C. 119 of U.S. Application No. 61/111,287 filed Nov. 4, 2008.

The present invention concerns the treatment and/or alleviation of inflammatory diseases of the central nervous system (CNS), such as but not limited to multiple sclerosis, and makes available compounds and methods for this use.

BACKGROUND

Cell migration is central to many processes in the human body, such as the immune response, but can also be a component of chronic inflammation. The migration of mononuclear cells to the CNS is believed to be one factor underlying the pathogenesis of inflammatory diseases of the CNS.

One example is multiple sclerosis (MS) which is an autoimmune disease that affects the CNS, i.e. the brain and spinal cord. MS is characterized by weakness, tremors, and visual impairments. Other symptoms are slurred speech and impaired mobility, e.g. that the patients drag their feet, stumble, and frequently drop objects. These symptoms may remain mild, come and go, or become crippling—but they tend to get progressively worse with age (Hafler, 2004). MS usually affects women more than men. The disorder most commonly begins between ages 20 and 40, but can strike at any age. The exact cause is not known, but MS is believed to result from damage to the myelin sheath, the protective material which surrounds nerve cells. It is a progressive disease, meaning that the damage gets worse over time. Inflammation destroys the myelin, leaving multiple areas of scar tissue (sclerosis). The inflammation occurs when the body's own immune cells attack the nervous system.

One important step in the pathogenesis of MS is the migration of cells to the CNS, wherein self-reactive T-cells, and B-cells together with monocytes mediate inflammation of the CNS, thereby causing demyelination of axons. Chemokines and their receptors are proposed to play a major role in the recruitment of these leukocytes to CNS. Thus, a reduction of chemokine receptors may be an effective strategy to prevent migration of destructive cells to CNS. Important chemokine receptors described in MS pathology are CCR5 (a receptor for chemotactic proteins such as RANTES and MIP-1alpha), CXCR3 (a receptor for chemotactic proteins such as IP-10 and MIG), and CCR2 (a receptor for chemotactic proteins such as MCP1-3) (Trebst C et al., 2009).

Another step that can lead the lymphocytes to enter into the parenchyma of the CNS is adhesion of CD49d (very late antigen, VLA-4 expressed on T-cells and B-cells) to their receptors on endothelial cells, and thereby transmigrate through the blood-brain barrier. A reduction of CD49d can reduce the transmigration and accumulation of immune cells in the CNS (Steinman L, 2009).

In healthy individuals, immune cells cannot pass through the CNS capillaries and venules into the CNS tissue because the walls of the capillaries in the CNS are different from those in the rest of the body in that they have very closely packed cells which do not allow the passage of immune cells. This special feature of the CNS vascular system is referred to as the blood-brain barrier (BBB). Vascular endothelial growth factor (VEGF) has been described to induce breakdown of the BBB, which in turn can exacerbate the inflammatory response in autoimmune disease of the CNS (e.g. MS) (Proescholdt M A et al., 2002). A reduction of VEGF is an effective strategy to prevent the increased vascular permeability of BBB and thereby reduce the influx of destructive cells into CNS.

The inflammation causes nerve impulses to slow down or become blocked, leading to the symptoms of MS. Repeated episodes, or flare ups, of inflammation can occur along any area of the brain and spinal cord.

Symptoms vary because the location and extent of each attack varies. Usually episodes which last days, weeks, or even months, alternate with periods of reduced or no symptoms (remission). Recurrence (relapse) is common although non-stop progression without periods of remission may also occur.

Patients diagnosed as having MS can expect one of four clinical courses of disease, each of which might be mild, moderate, or severe:

1. Relapsing-Remitting

Characteristics: People with this type of MS experience clearly defined flare-ups (also called relapses, attacks, or exacerbations). These are episodes of acute worsening of neurological function. They are followed by periods of partial or complete recovery (remissions) free of disease progression.

Frequency: Most common form of MS at time of initial diagnosis. Approximately 85% of patients.

2. Primary-Progressive

Characteristics: People with this type of MS experience a slow but nearly continuous worsening of their disease from the onset, with no distinct relapses or remissions. However, there are variations in rates of progression over time, occasional plateaus, and temporary minor improvements.

Frequency: Relatively rare. Approximately 10% of patients.

3. Secondary-Progressive

Characteristics: People with this type of MS experience an initial period of relapsing-remitting MS, followed by a steadily worsening disease course with or without occasional flare-ups, minor recoveries (remissions), or plateaus.

Frequency: 50% of people with relapsing-remitting MS developed this form of the disease within 10 years of their initial diagnosis, before introduction of the "disease-modifying" drugs. Long-term data are not yet available to demonstrate if this is significantly delayed by treatment.

4. Progressive-Relapsing

Characteristics: People with this type of MS experience a steadily worsening disease from the onset but also have clear acute relapses (attacks or exacerbations), with or without recovery. In contrast to relapsing-remitting MS, the periods between relapses are characterized by continuing disease progression.

Frequency: Relatively rare. Approximately 5% of patients.

There is no consensus within the scientific community as to what triggers an attack. Patients with MS typically have a higher number of immune cells than a healthy person, which suggests that an immune response might play a role. The most common theories point to a virus or genetic defect, or a combination of both. There also appears to be a genetic link to the disease. MS is more likely to occur in northern Europe, the northern United States, southern Australia, and New Zealand than in other areas. Geographic studies indicate there may be an environmental factor involved. People with a family history of MS and those who live in a geographical area with a higher incidence rate for MS have a higher risk of the disease.

Medications such as interferon-beta, glatiramer acetate, and mitoxantrone can reduce the frequency and severity of attacks in people with relapsing-remitting MS and may reduce or delay future disability. Interferon-beta and mitoxantrone may also slow the progression of secondary progressive MS.

Treatment with interferon-beta or glatiramer acetate should begin as soon as relapsing-remitting MS has been diagnosed. Most specialists now agree that permanent damage to the nervous system may occur early on, even while the symptoms are still quite mild. Early treatment may help prevent or delay some of this damage.

Interferon beta treatment is however accompanied by several adverse effects. The most frequent adverse effects are flu-like symptoms: increased body temperature, feeling ill, fatigue, headache, muscle pain, convulsion, dizziness, hair thinning, and depression. Erythema, pain and hardness on the spot of injection are also frequently observed. Interferon therapy causes immunosuppression and can result in some infections manifesting in unusual ways.

Also corticosteroids may be given during a relapse to reduce inflammation and shorten the attack. The potent effect of corticosteroids can result in serious side effects which mimic Cushing's disease, a malfunction of the adrenal glands resulting in an overproduction of cortisol. The list of potential side effects is long and includes: increased appetite and weight gain; deposits of fat in chest, face, upper back, and stomach; water and salt retention leading to swelling and edema; high blood pressure; diabetes; black and blue marks; slowed healing of wounds; osteoporosis; cataracts; acne; muscle weakness; thinning of the skin; increased susceptibility to infection; stomach ulcers; increased sweating; mood swings; psychological problems such as depression; and adrenal suppression.

In 2004, the FDA approved the use of a monoclonal antibody (natalizumab, Tysabri®, Biogen Idec Inc., Cambridge, Mass., USA, and Elan Pharmaceuticals, Inc., Dublin, Ireland) for the treatment of patients with relapsing forms of MS (FDA News P04-107, Nov. 23, 2004).

While generally well tolerated, natalizumab is occasionally associated with severe adverse effects. Antibody therapy in general is costly, and there is a need for improvements inter alia with regards to efficacy.

Currently, a number of other monoclonal antibodies are being investigated for MS, including some that are already in use in other conditions. These include ocrelizumab (Genentech/Hoffmann-La Roche) daclizumab (Biogen Idec, Inc.), alemtuzumab (Campath®, MabCampath®, Bayer Schering, BTG, Genzyme, Millenium), and rituximab (Rituxan®, MabThera®, Genentech, Hoffmann-La Roche, Biogen Idec Inc.)

WO 2006/065751 concerns a CpG oligonucleotide prodrug that includes a thermolabile substituent on at least one nucleotide thereof. Therapeutic methods of using such thermolabile CpG oligonucleotide prodrugs are described. The induction of cytokines, in particular interferons, e.g. interferon-alpha, interferon-beta, or interferon-gamma is disclosed.

WO 2006/027776 concerns methods for regulating an AChE-associated biological pathway having a miRNA component, the methods comprising subjecting the AChE-associated biological pathway to an agent capable of regulating a function of the miRNA, thereby regulating the AChE-associated biological pathway. Said agents include modified polynucleotide sequences.

WO 2007/095316 relates generally to immunostimulatory nucleic acids, compositions thereof and methods of using the immunostimulatory nucleic acids. In particular the invention relates to palindrome-containing immunostimulatory nucleic acids and the use of these nucleic acids in treating disease.

WO 2004/016805 discloses a class of soft or semi-soft CpG immunostimulatory oligonucleotides that are useful for stimulating an immune response.

In summary, there is a need for improving existing therapies for MS, with the aim of improving efficacy, as well as reducing cost and adverse effects. There is also a need for developing new treatment strategies for the battle against MS.

SUMMARY

The present inventors realized that the existing approaches to treat or alleviate MS were insufficient in view of both the results of treatment, the cost of treatment, and the occurrence of adverse effects. The inventors set out to identify novel compounds useful for the treatment and/or alleviation of MS, and to develop methods of treatment having improved efficacy and reduced adverse effects on the patients. Other problems underlying the invention, as well as advantages associated with the invention, will become evident to the skilled person upon study of the description, examples, and claims, incorporated herein by reference.

The inventors surprisingly found that specific oligonucleotide sequences were effective to inhibit or reduce the influx of autoaggressive cells to the central nervous system by down-regulating the expression of specific cell surface markers. The inventions and embodiments are as set out in the enclosed claims, incorporated herein by reference.

SHORT DESCRIPTION OF THE DRAWINGS

Figure 2:
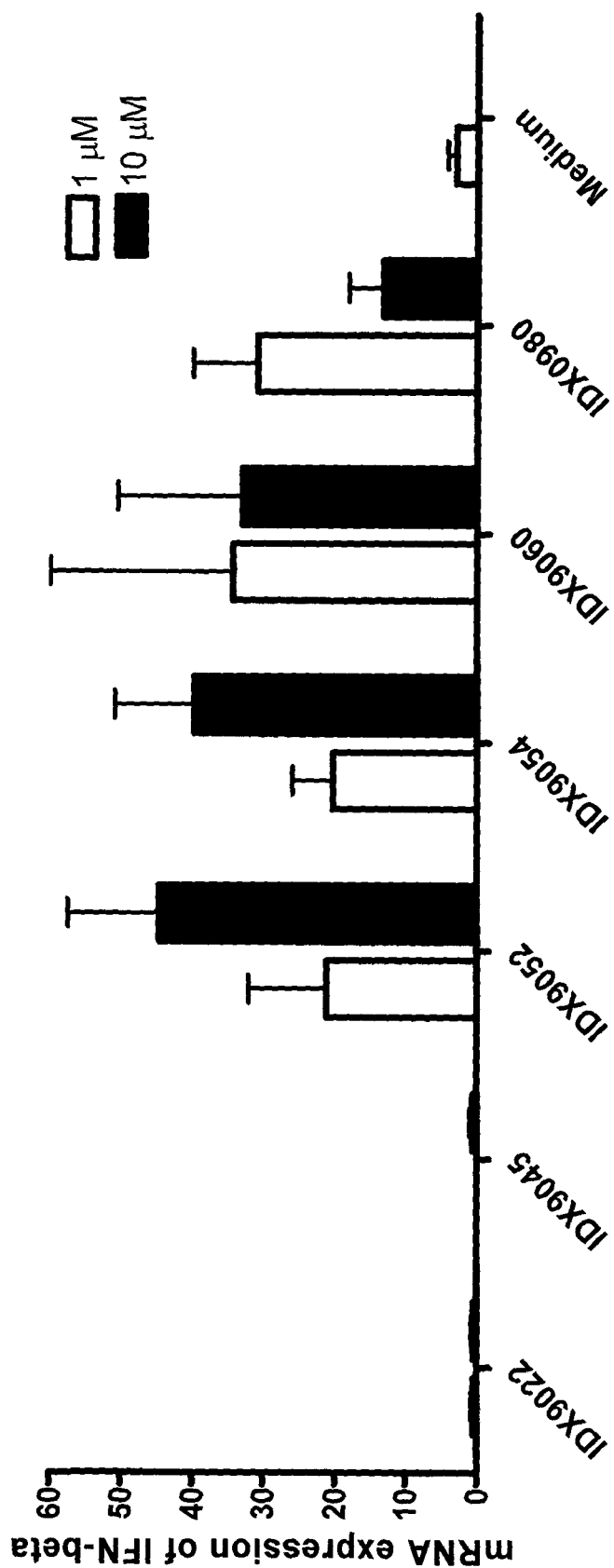
Figure 3:
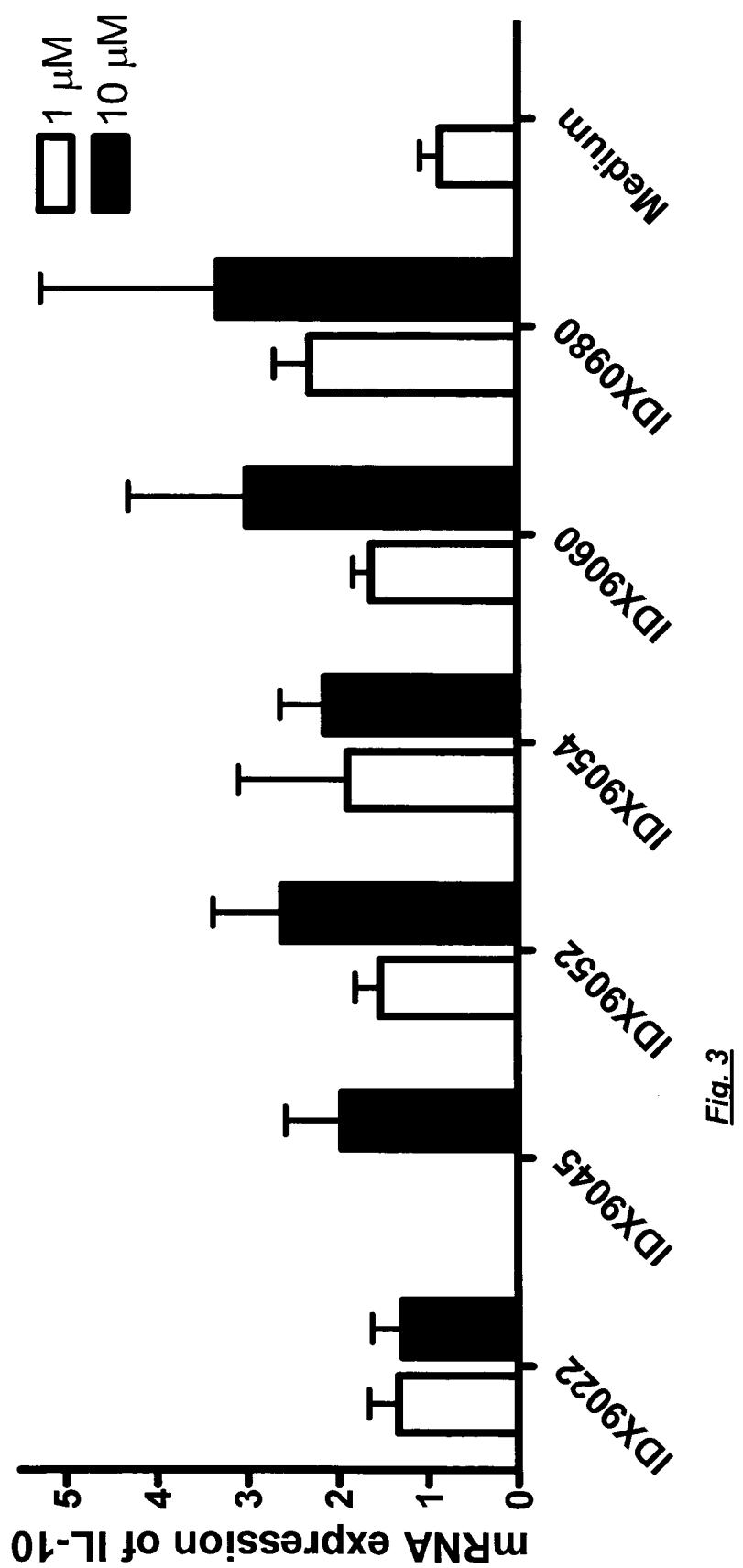

In the following detailed description, reference will be made to the attached drawings in which;

FIGS. 1-3 are bar diagrams, showing normalized relative mRNA expression of IFN-alpha (FIG. 1), IFN-beta (FIG. 2), and IL-10 (FIG. 3) in rat splenocytes stimulated with the inventive compounds and cultured for 24 hours. Values were normalized to the mean RQ value of the samples that were stimulated with medium only. Data are shown as means±SD of splenocytes derived from 6 spleens.

Figure 4:
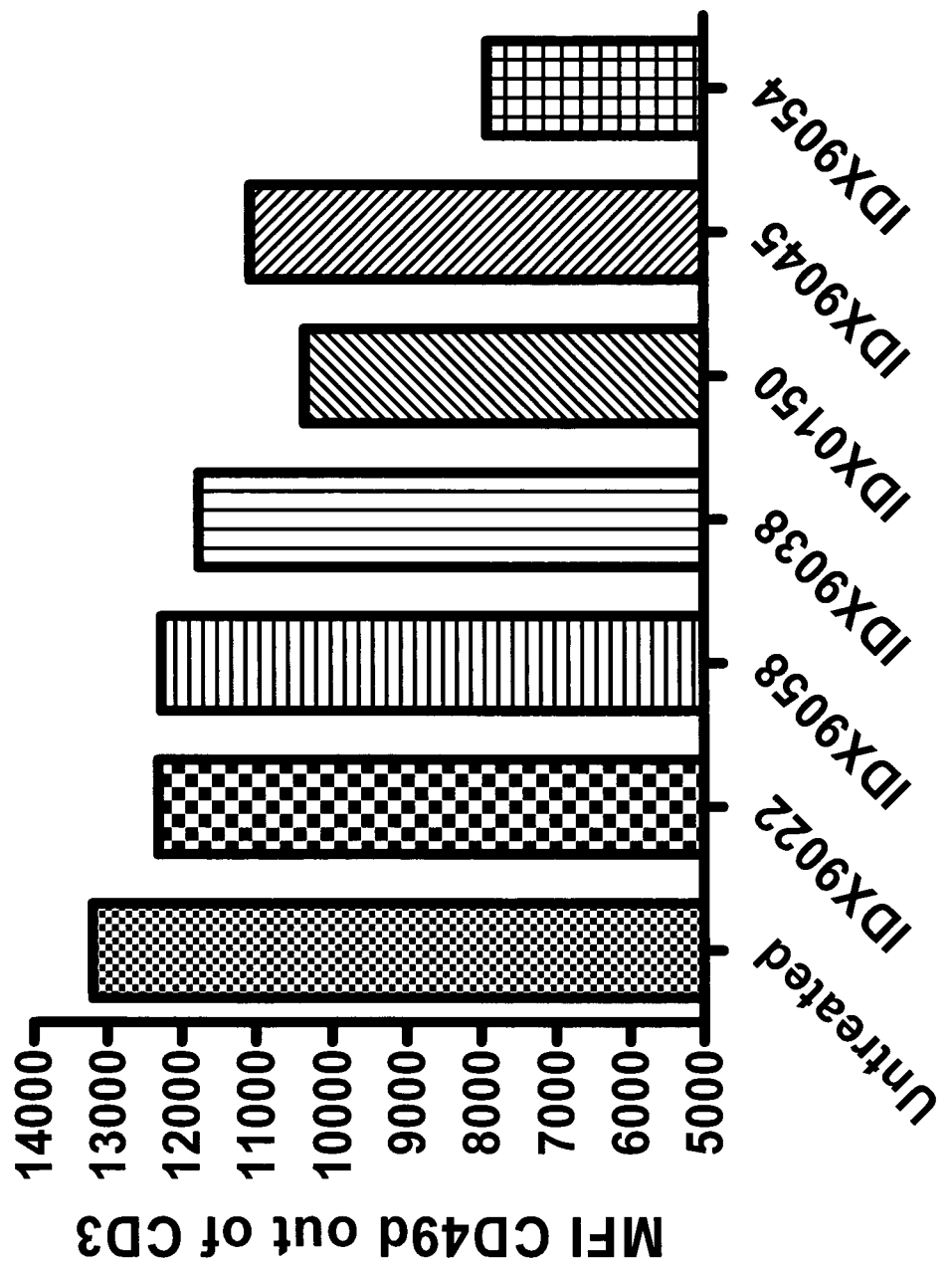

FIG. 4 is a bar diagram showing the expression of CD49d (MFI) in splenocytes from DA rat (n=3). Splenocytes ($2\times10^6$/ml) left untreated or stimulated (10 μM) with drugs. The inventive compounds were able to down-regulate CD49d expressed on CD3 expressing cells after 48 h incubation as analyzed by FACS.

Figure 5:
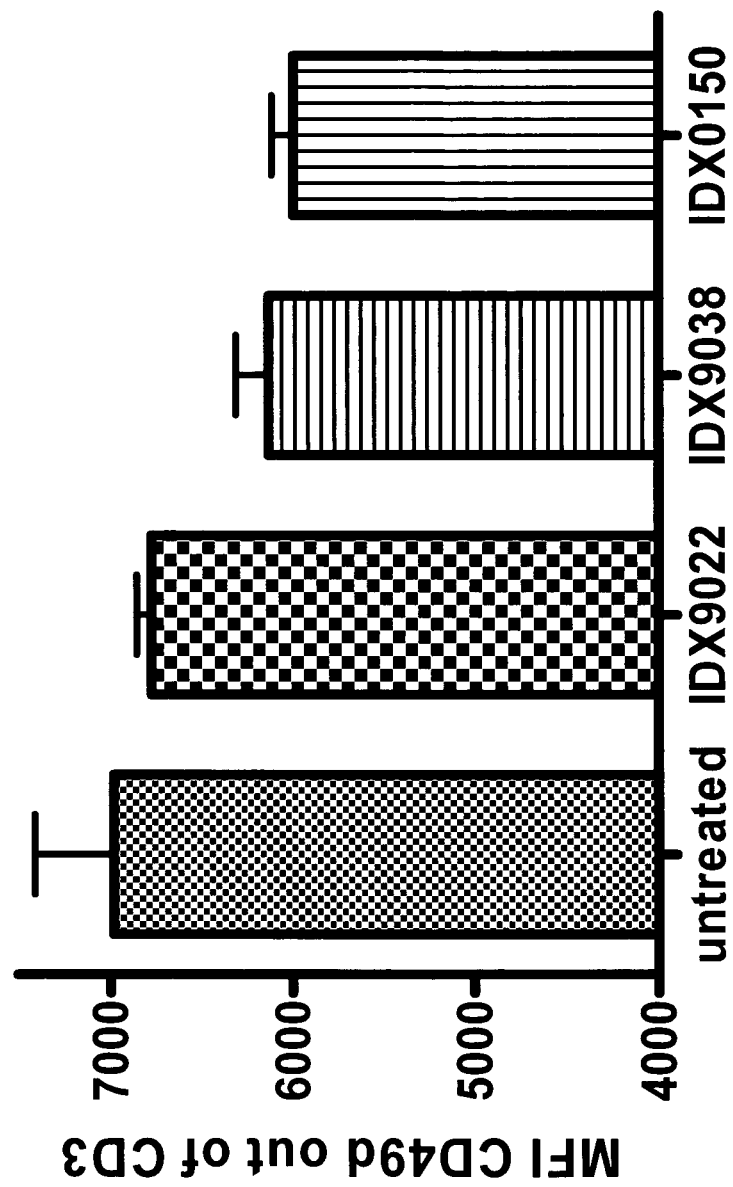

FIG. 5 shows the expression of CD49d (MFI) in PBMC from DA rat. PBMC ($2\times10^6$/ml) left untreated or stimulated (10 μM) with drugs. The inventive compounds were able to down-regulate CD49d expressed on CD3 expressing cells after 48 h incubation as analyzed by FACS.

Figure 6:
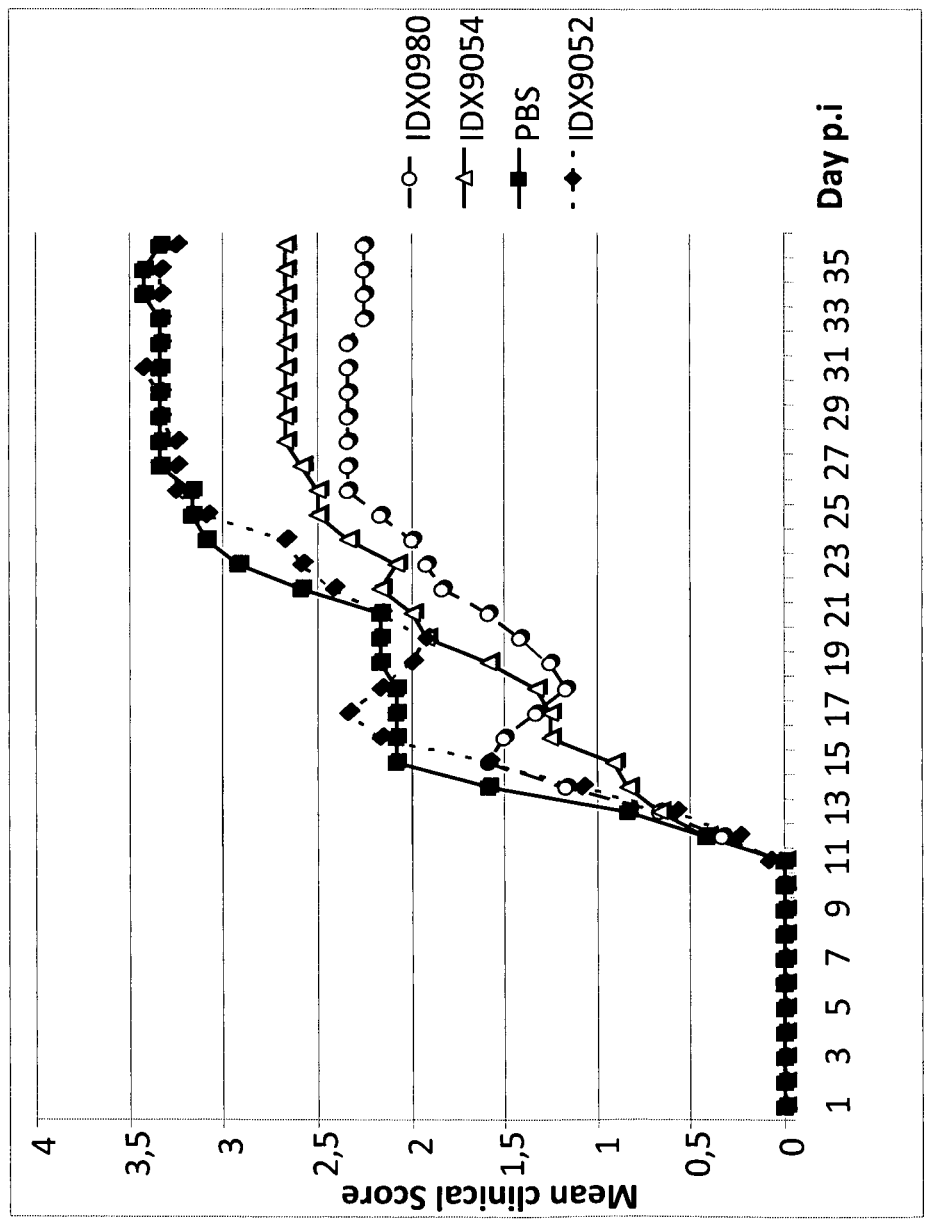

FIG. 6 is a graph, illustrating the mean clinical score of MOG-induced EAE in DA rats (female) showing therapeutic effect of oligonucleotides and vehicle (PBS). Twelve rats in each group were all immunized with rat MOG in Incomplete Freund's adjuvant (IFA) at day 0. IDX9052, IDX9054, IDX0980 and vehicle were administered before the peak of the first attack (day 9 and day 15), and during the peak of the first attack (day 20). Hundred fifty μg of drugs were administered s.c. in a total volume of 100 μl.

Figure 7:
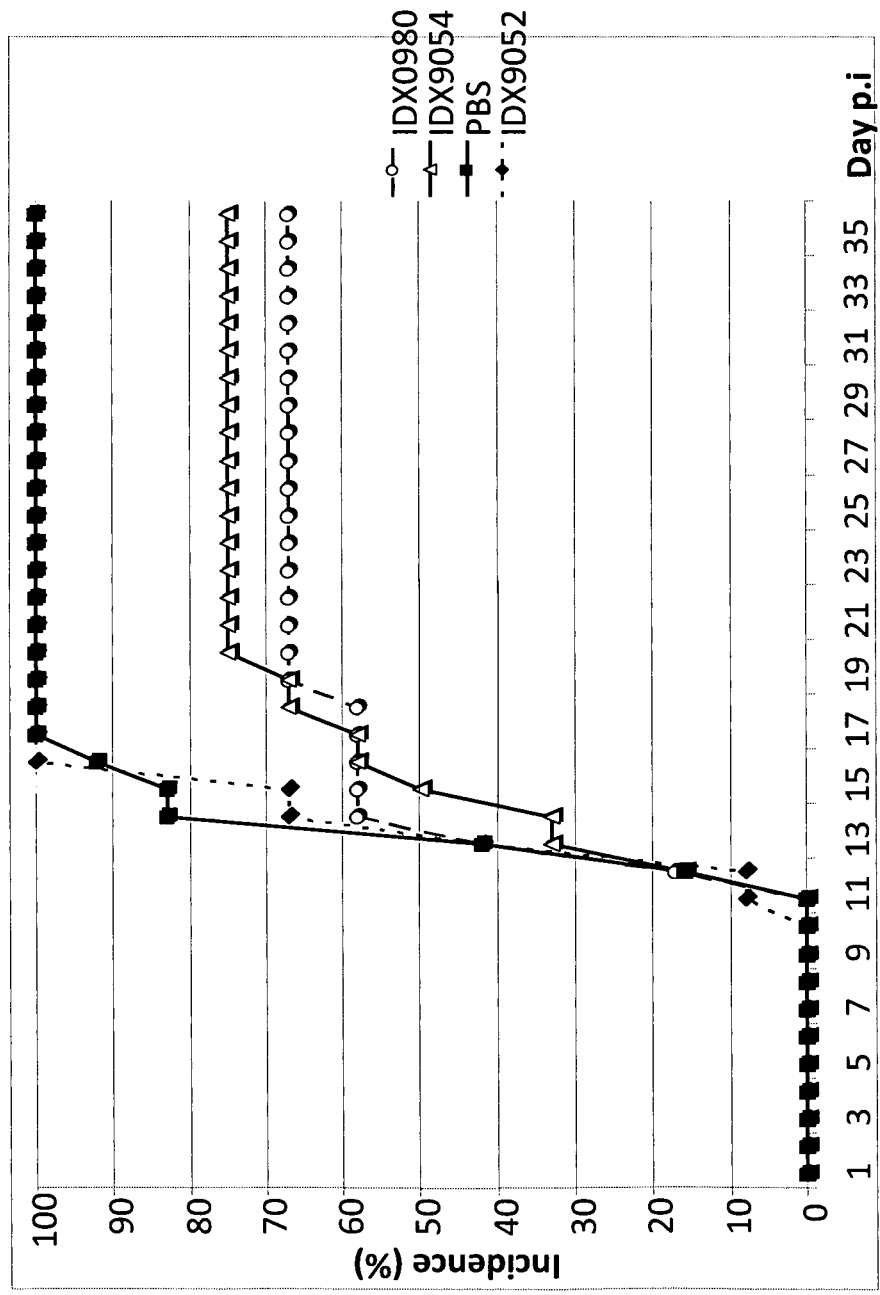

FIG. 7 is a graph, showing the incidence of MOG-induced EAE in DA rats. Disease severity was reduced in rats treated with IDX0980 and IDX9054 compared to PBS and IDX9052 treated groups.

Figure 8:
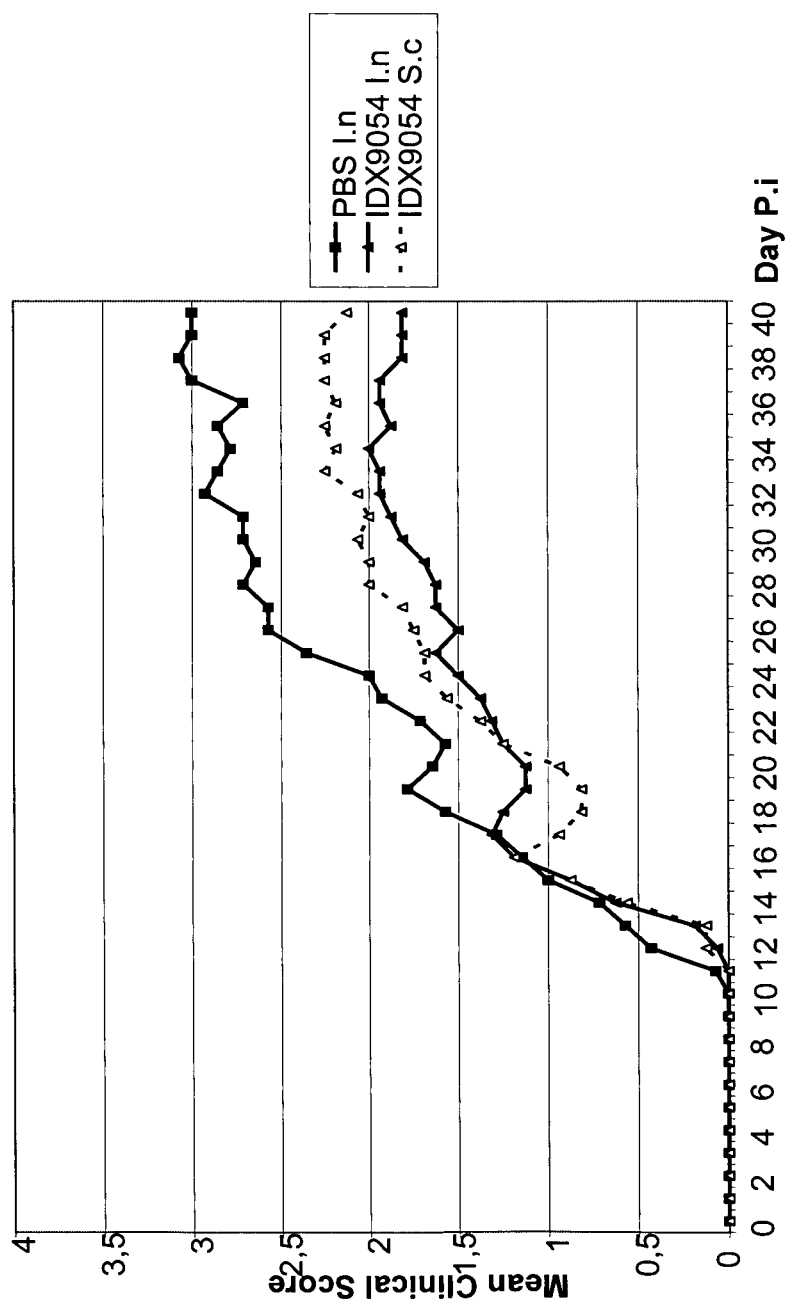

FIG. 8 illustrates the mean clinical score of MOG-EAE in DA rats showing therapeutic effect of oligonucleotides and vehicle (PBS). 16 rats in each group were all immunized with rat MOG in Incomplete Freund's adjuvant (IFA) at day 0. IDX9054 and vehicle were administered before the peak of the first attack (day 9 and day 15), and during the peak of the first attack (day 20). 150 µg of drugs were administered in a total volume of 100 µl s.c and 40 µl i.n. PBS treated group was only treated i.n.

Figure 9:
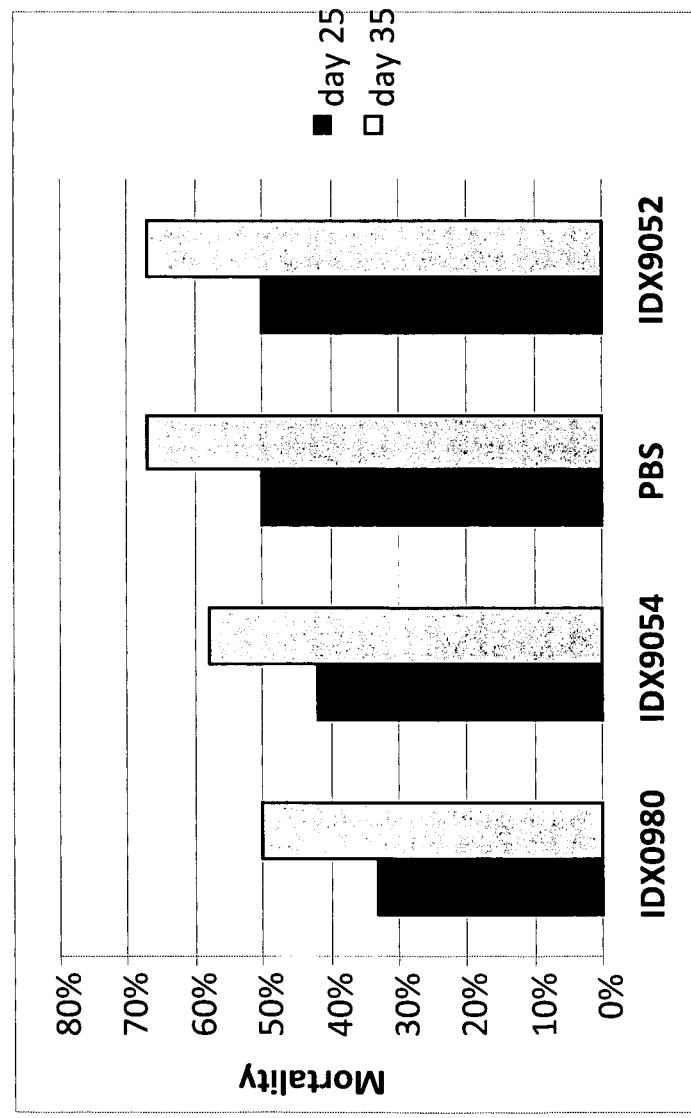

FIG. 9 shows the mortality of MOG-EAE in DA rats. Reduced mortality in both IDX0980 and IDX9054 treated groups as compared to PBS and IDX9052 treated group. The rats either die of the disease or were killed according to ethical regulations. Data are presented at both day 25 and 35.

Figure 10:
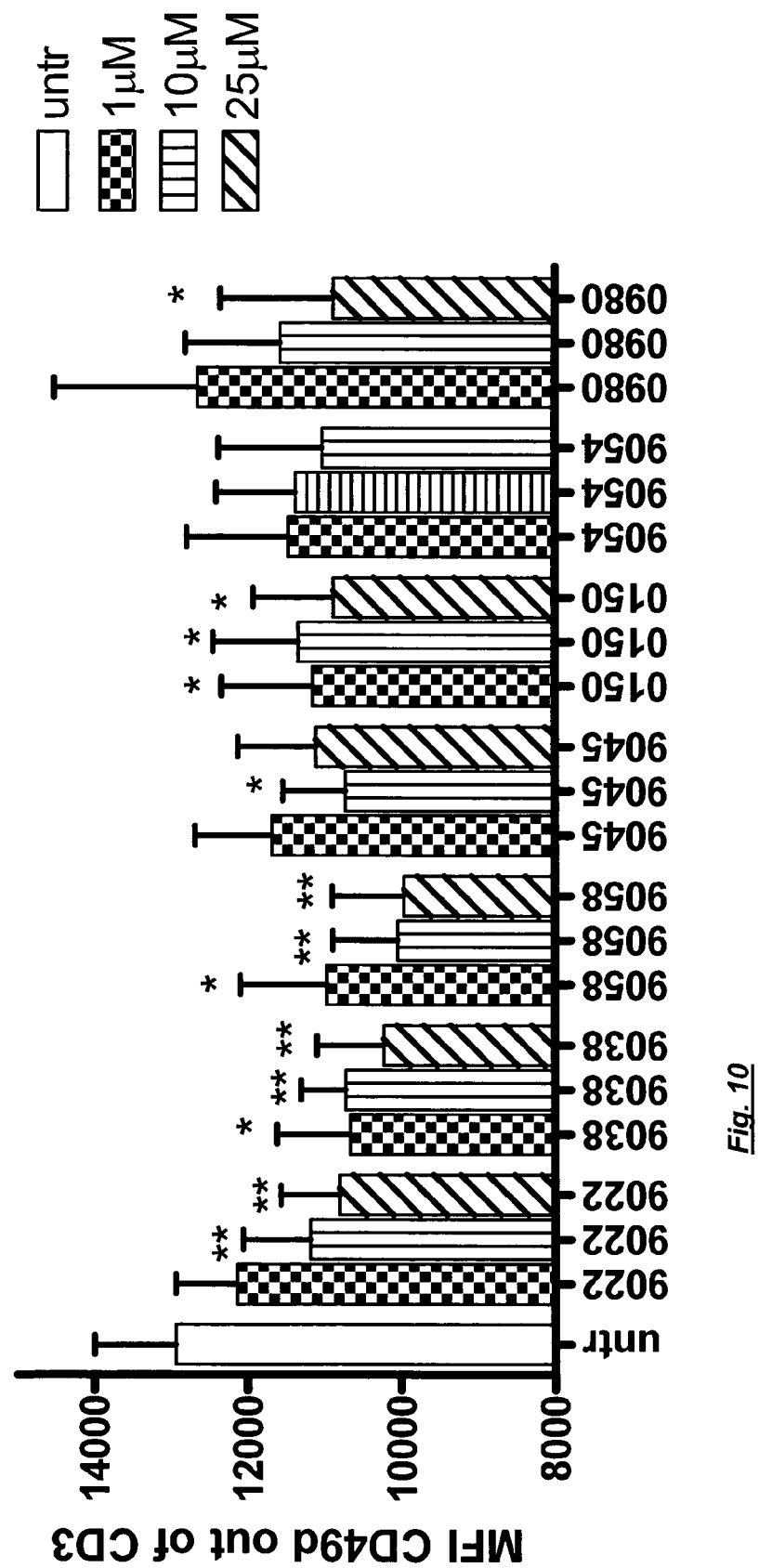

FIG. 10 shows the expression of CD49d on CD3 positive cells isolated from RRMS patients (n=9). PBMC ($2\times10^6$/ml) left untreated or stimulated (1, 10 and 25 µM) with drugs. The oligonucleotides were able to down regulate expression of CD49d on CD3 positive T cells after 48 h incubation as analyzed by FACS. Error bars indicate SEM, *P<0.05, P<0.01, *P<0.001 as analyzed by nonparametric T test, Wilcoxon matched pair test.

Figure 11:
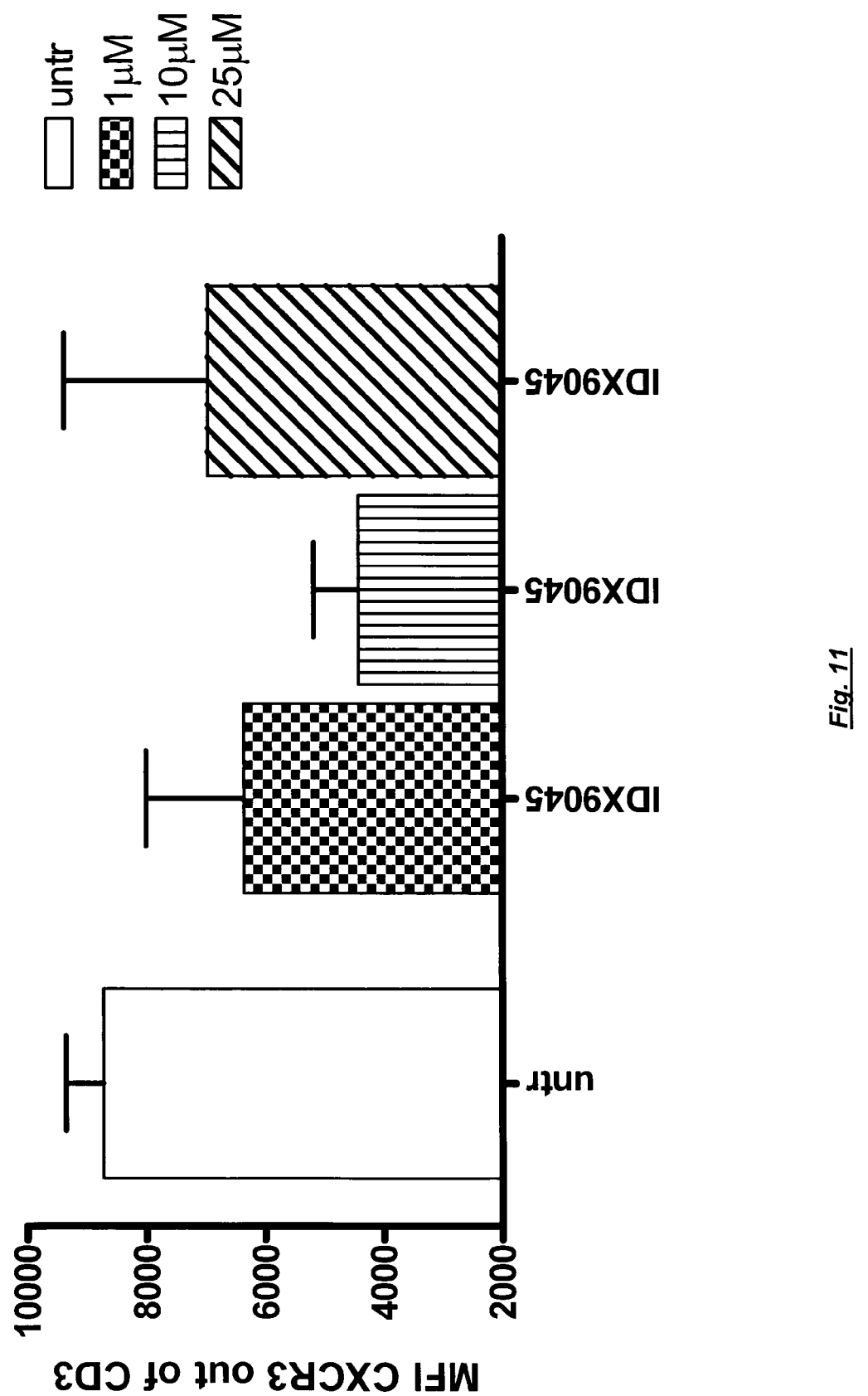

FIG. 11 shows the expression of CXCR3 (CD183) on CD3 positive cells isolated from RRMS patients. PBMC ($2\times10^6$/ml) left untreated or stimulated (1, 10 and 25 µM) with drugs. The inventive compound was able to down-regulate the expression of CXCR3 on CD3 positive T cells after 48 h incubation as analyzed by FACS.

Figure 12:
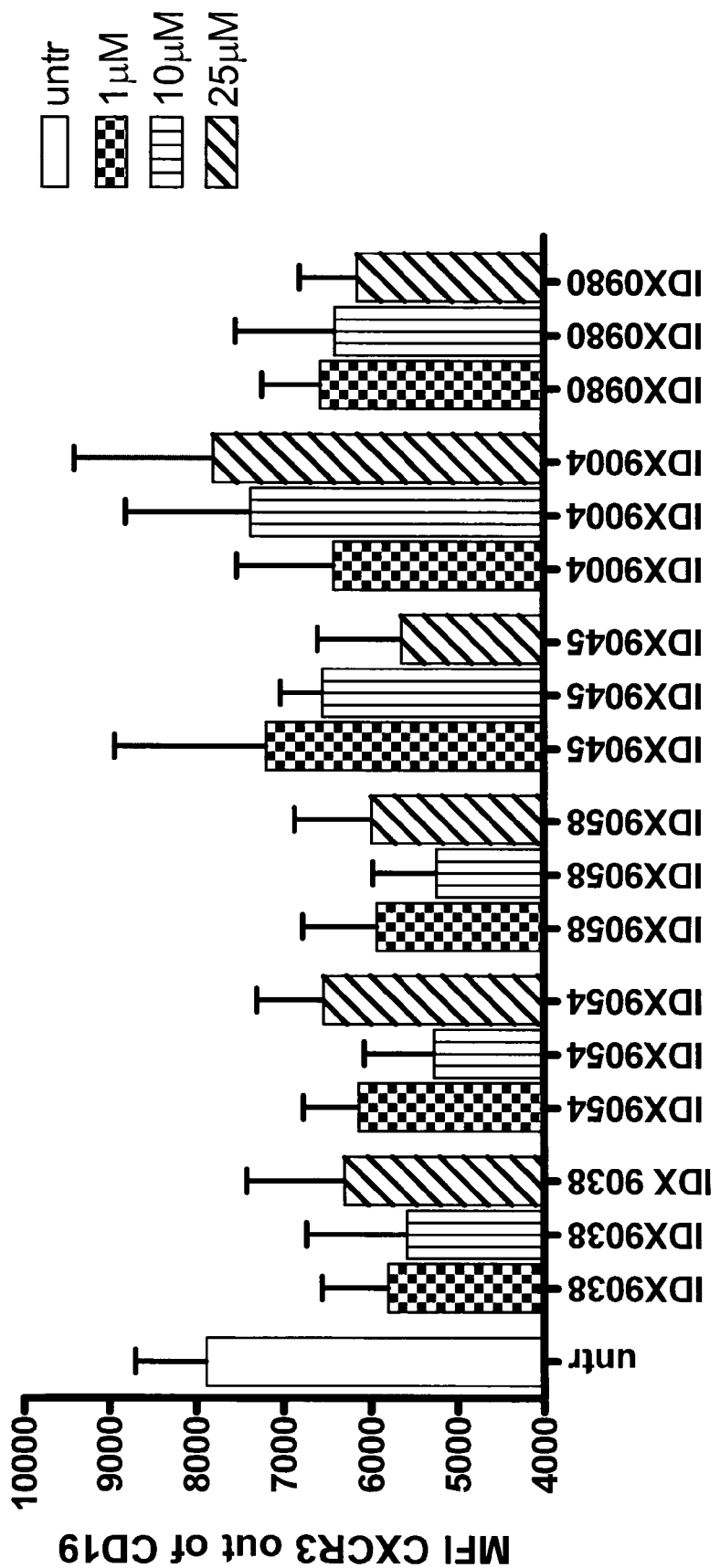

FIG. 12 shows the expression of CXCR3 (CD183) on CD19 positive cells isolated from RRMS patients. PBMC ($2\times10^6$/ml) left untreated or stimulated (1, 10 and 25 µM) with drugs. The oligonucleotides were able to down-regulate expression of CXCR3 on CD19 positive cells after 48 h incubation as analyzed by FACS.

Figure 13:
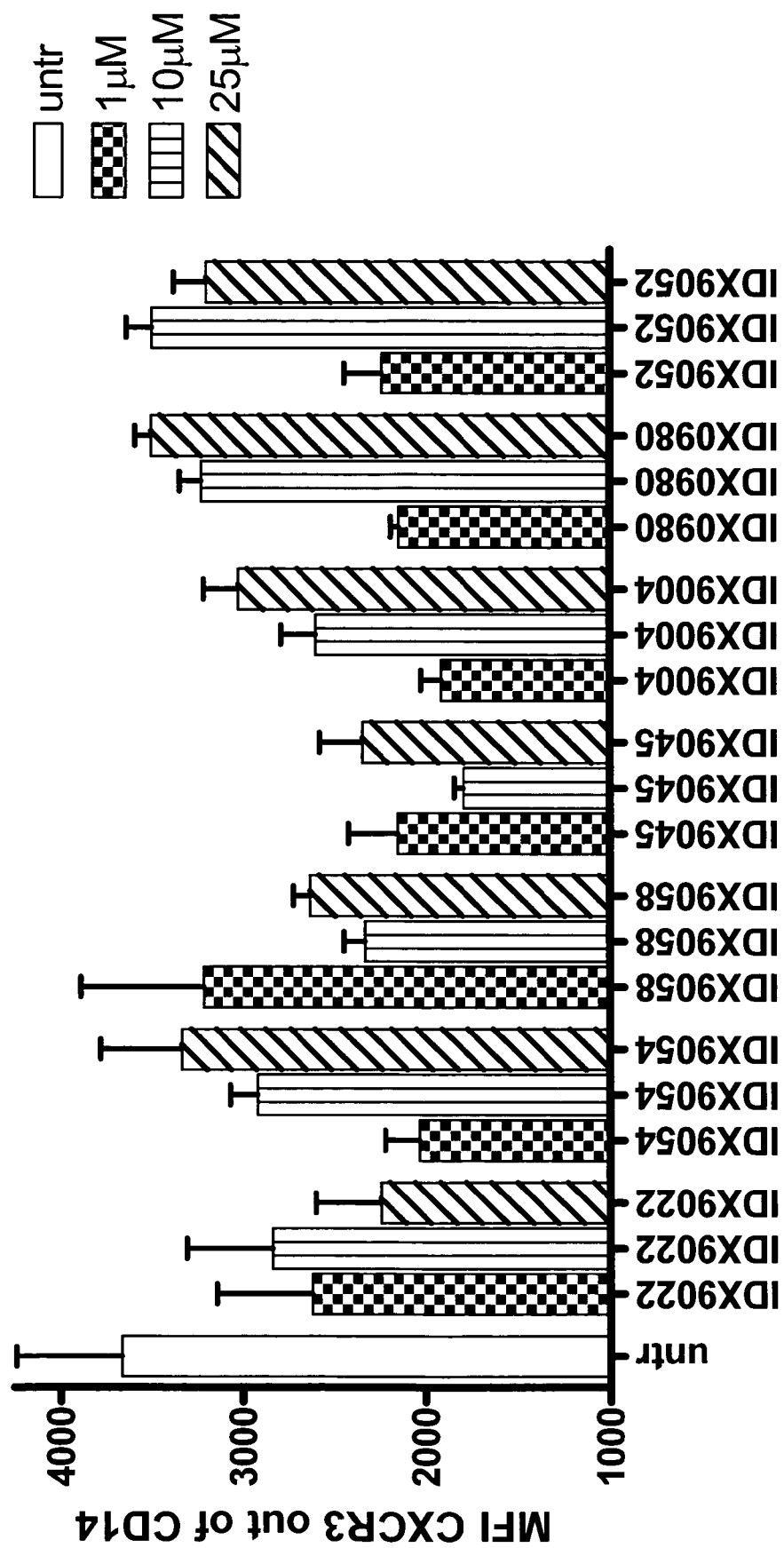

FIG. 13 shows the expression of CXCR3 (CD183) on CD14 positive cells isolated from RRMS patients. PBMC ($2\times10^6$/ml) left untreated or stimulated (1, 10 and 25 µM) with drugs. The oligonucleotides were able to down-regulate expression of CXCR3 on CD14 positive cells after 48 h incubation as analyzed by FACS.

Figure 14:
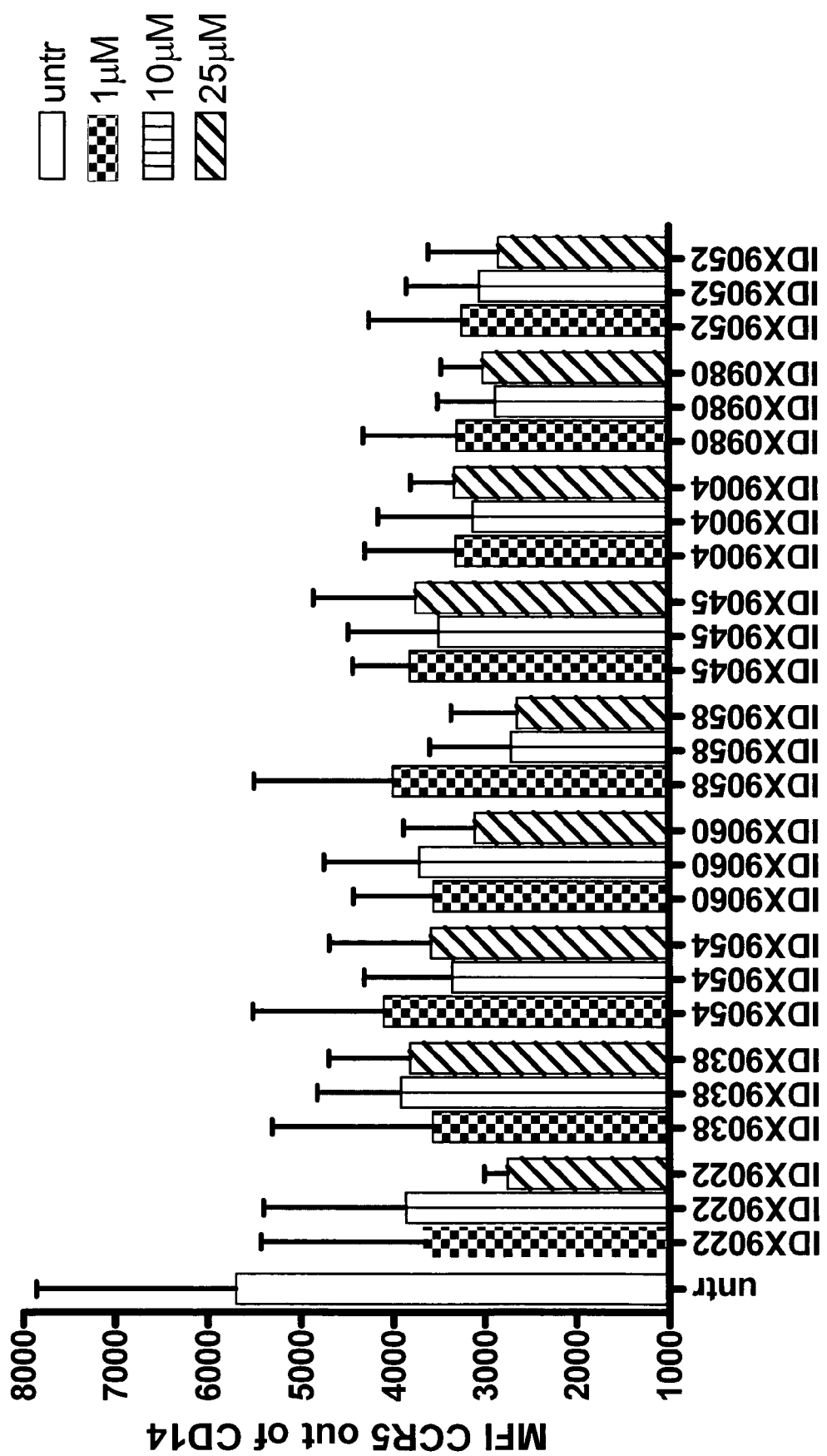

FIG. 14 shows the expression of CCR5 (CD195) on CD14 positive cells isolated from RRMS patients. PBMC ($2\times10^6$/ml) left untreated or stimulated (1, 10 and 25 µM) with drugs. The oligonucleotides were able to down-regulate expression of CCR5 on CD14 positive cells after 48 h incubation as analyzed by FACS.

Figure 15A:
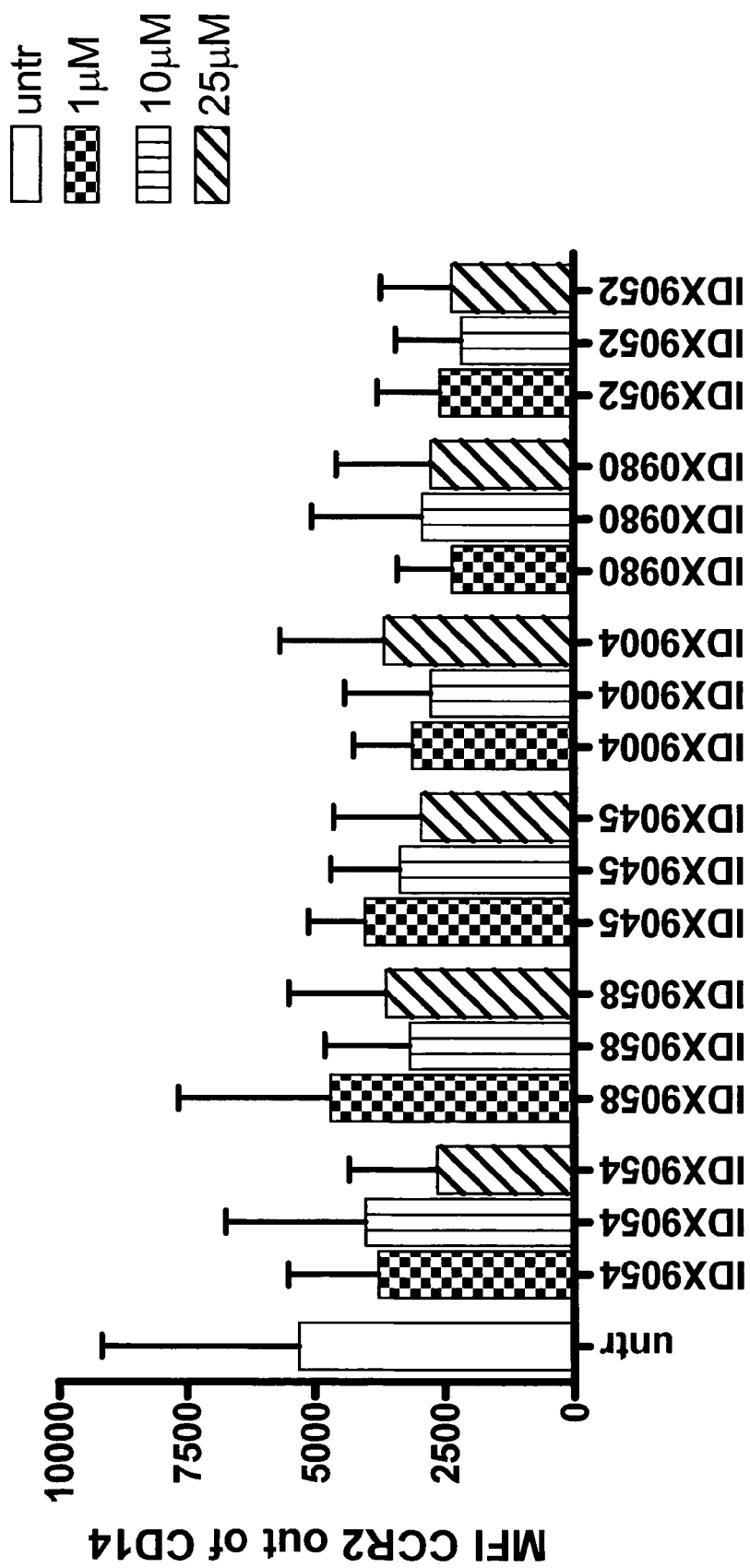
Figure 15B:
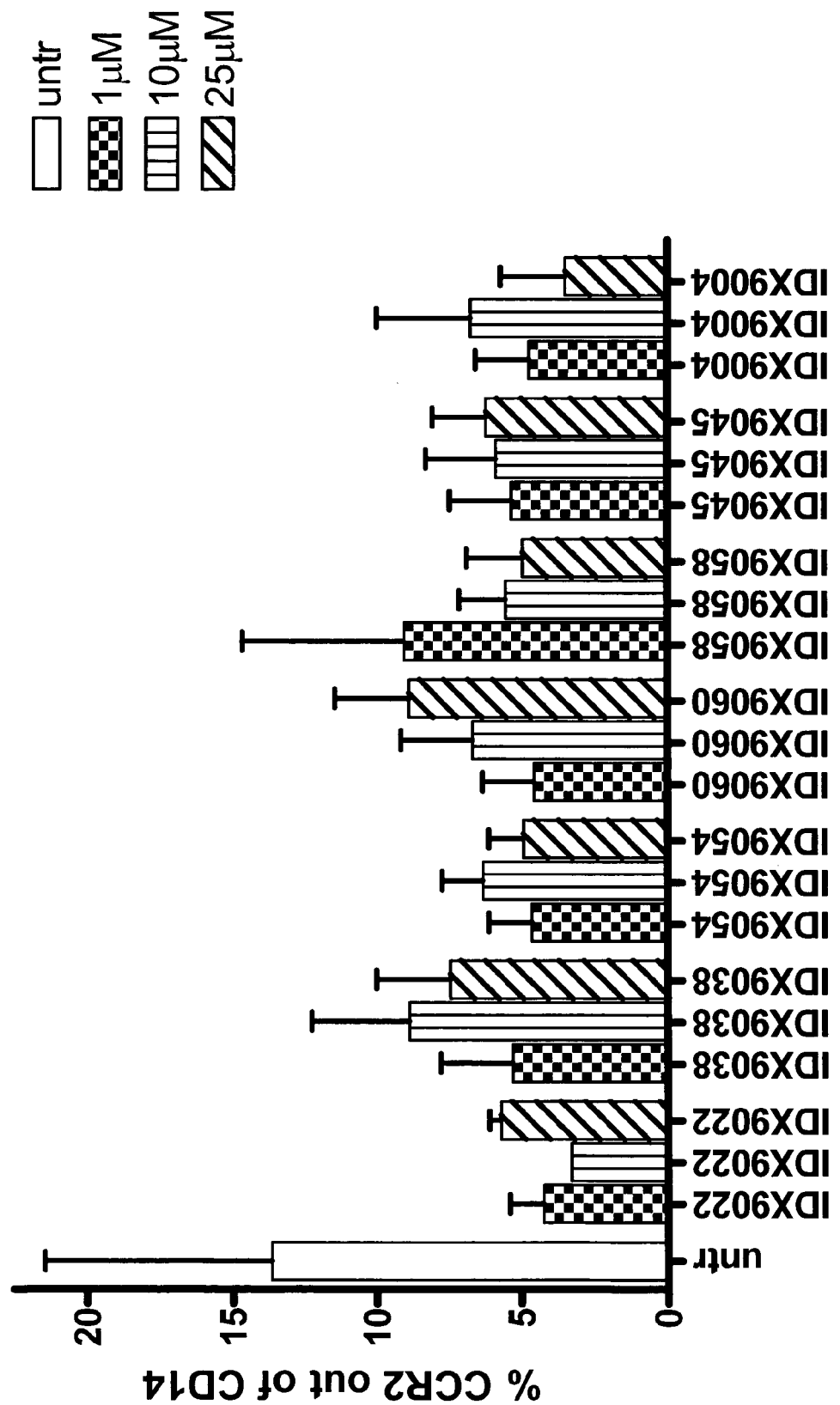

FIG. 15 shows the expression of CCR2 (CD192) on CD14 positive cells isolated from RRMS patients in MFI (A) or % (B), respectively. PBMC ($2\times10^6$/ml) left untreated or stimulated (1, 10 and 25 µM) with drugs. The oligonucleotides were able to down-regulate expression of CCR2 on CD14 positive cells after 48 h incubation as analyzed by FACS.

FIG. 16 Shows migration of cells towards MCP-1 and RANTES. PBMCs $0.5\times10^6$ (A) or $0.250\times10^6$ (B) from two RRMS patients were incubated with the inventive compounds IDX9045, IDX9054, IDX0980 (1, 10 and 25 µM) or left untreated for 48 h. Cells were then used in QCM migration assay in order to analyze migration towards MCP-1 and RANTES. Both experiments showed reduced migration of cells treated with inventive compounds compared to untreated cells.

Figure 17:
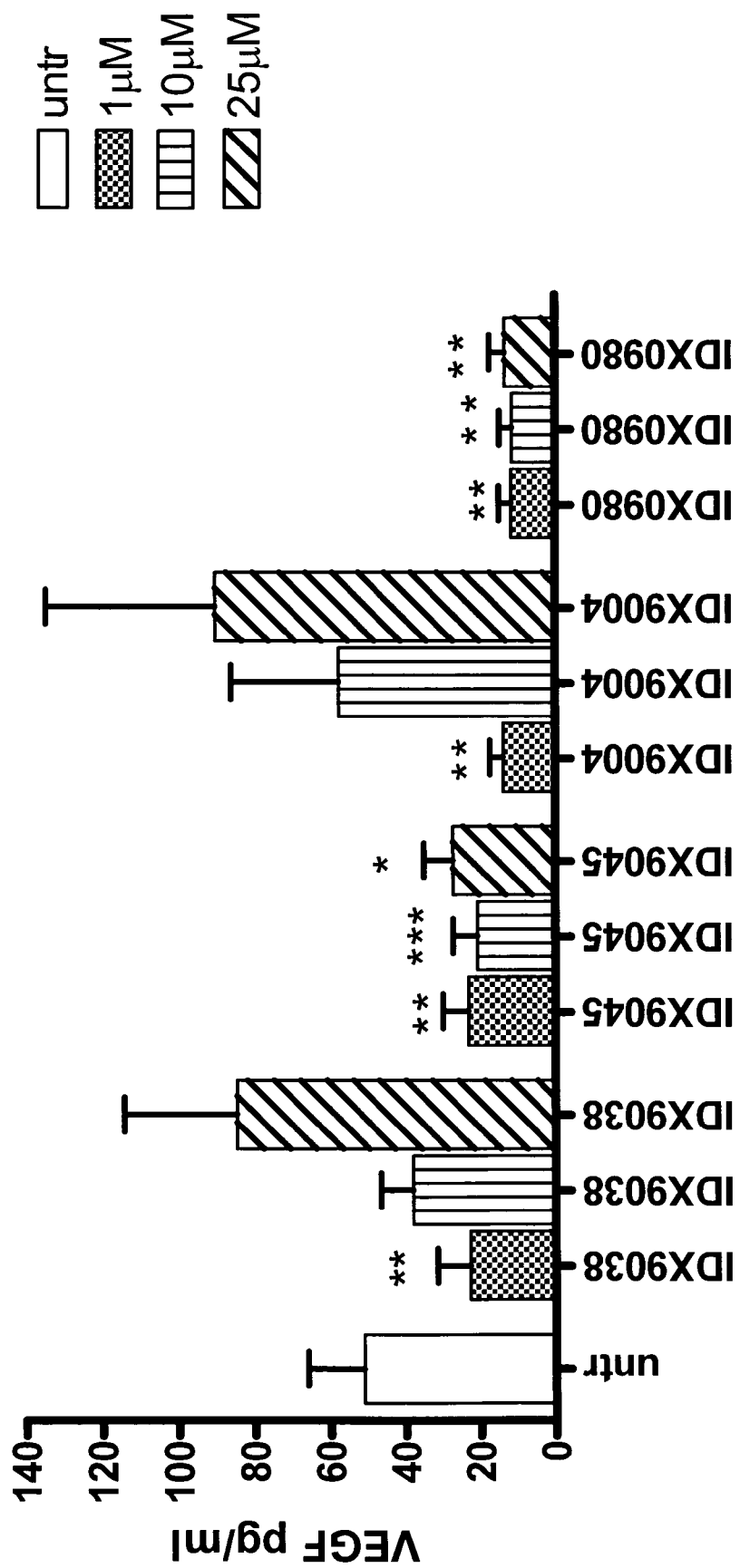

FIG. 17 shows the expression of VEGF in supernatant from RRMS patients (n=6-11). PBMC ($2\times10^6$/ml) left untreated or stimulated (1, 10 and 25 µM) with drugs. The oligonucleotides were able to down-regulate VEGF in supernatant from the stimulated cells after 48 h incubation as analyzed by CBA. Error bars indicate SEM, *P<0.05, P<0.01, *P<0.001 as analyzed by nonparametric T test, Wilcoxon matched pair test.

Figure 18:
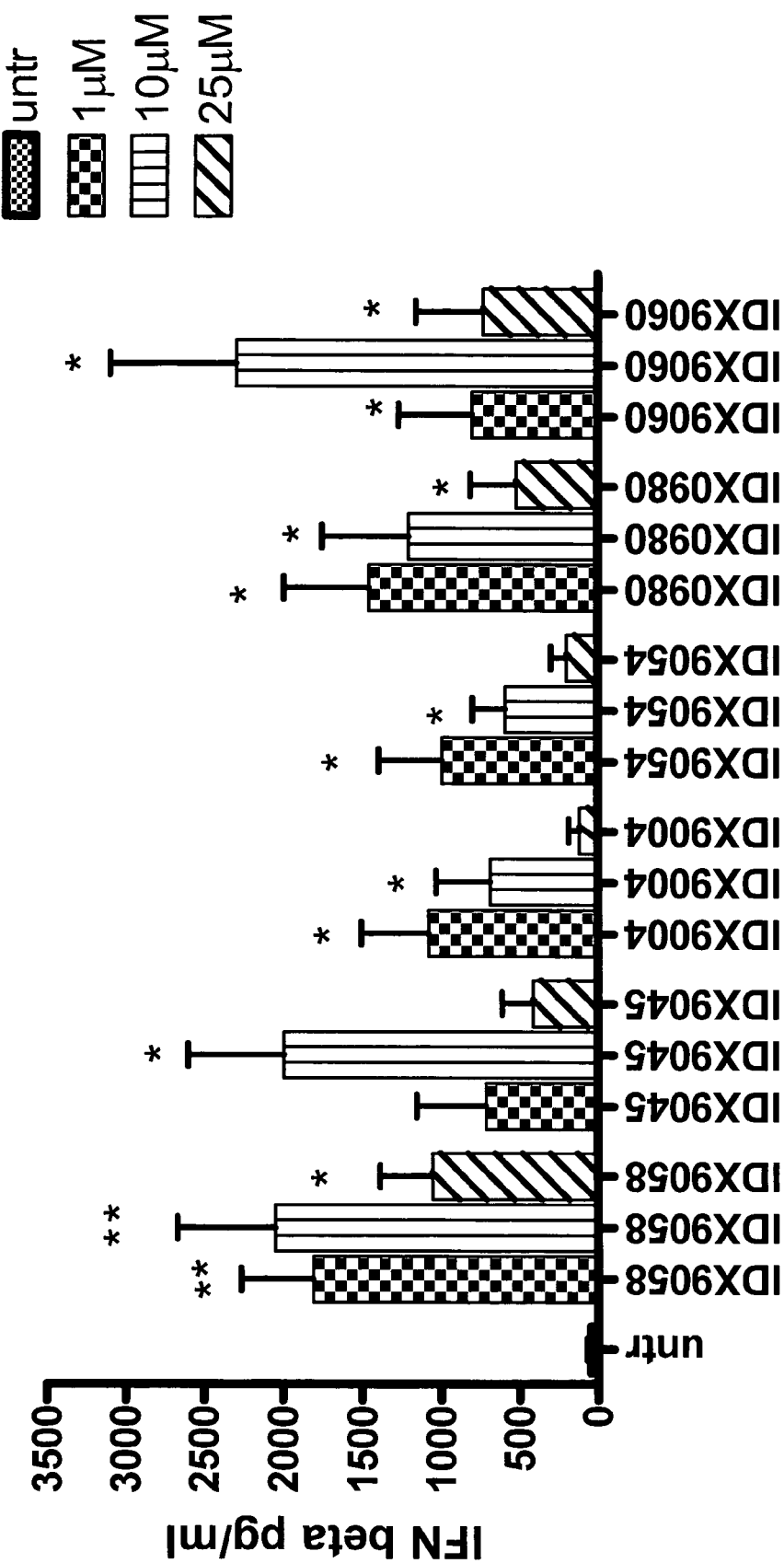

FIG. 18 shows the induction of IFN-beta in PBMC isolated from RRMS patients. PBMCs ($2\times10^6$/ml) from different RRMS patients (n=6) were stimulated with three different concentrations (1, 10 and 25 µM) of oligonucleotides. IFN-beta-production was analyzed after 48 h incubations using IFN-beta ELISA kit.

DESCRIPTION

The following description is of the best mode presently contemplated for carrying out the invention. This description is not to be taken in a limiting sense, but is made solely for the purpose of describing the general principles of the invention. The scope of the invention should be determined with reference to the claims.

Before the invention is described in detail, it is to be understood that this invention is not limited to the particular compounds described or process steps of the methods described as such compounds and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a sequence" includes more than one such sequence, and the like.

Further, the term "about" is used to indicate a deviation of +/−2% of the given value, preferably +/−5% and most preferably +/−10% of the numeric values, when applicable.

The term "influx" as used in the expression "the influx of autoaggressive cells to the central nervous system" is intended to mean the accumulation of autoaggressive cells in the central nervous system, and includes the steps of migration, adhesion, and transmigration of mononuclear cells, in particular T-cells, B-cells, and monocytes.

The invention makes available specific novel nucleotides, i.e. the isolated oligonucleotide sequences according to any one of SEQ ID NO 1-8. See Table 1, which correlates the SEQ ID No:s, the internal references and the sequences.

TABLE 1

Oligonucleotides

| SEQ ID NO | Seq 5'-3' | IDX-No |
|---|---|---|
| 1 | G*G*G*TCGCAGC*T*G*G | IDX9045 |
| 2 | G*G*G*GTCGTCTGC*G*G*G | IDX9054 |
| 3 | T*C*G*TCGTTCGGCCGATCG*T*C*C | IDX9038 |
| 4 | G*G*G*GTCGCAGCT*G*G*G | IDX9004 |
| 5 | G*G*G*GTCGTCTG*C*G*G | IDX9052 |
| 6 | T*C*G*TCGTTCTGCCATCGTC*G*T*T | IDX9022 |
| 7 | G*A*T*CGTCCGTCGG*G*G*G | IDX9058 |
| 8 | G*G*G*GATCGTCCG*G*G*G | IDX9060 |
| 9 | G*G*A*ACAGTTCGTCCAT*G*G*C | IDX0150 |
| 10 | G*G*GGGACGATCGTCG*G*G*G*G*G | IDX0980 |

*= phosphorothioate modification

The above sequences SEQ ID NO 1-8 have been designed by the inventors, and are to the best knowledge of the inventors, not previously known. SEQ ID NO 10, although known for medical use (see below), is to the best knowledge of the inventors not previously known for use in the treatment of MS.

SEQ ID NO 9 (IDX0150) is known from U.S. Pat. No. 6,498,147, and has been successfully tested in phase II clinical trials for the treatment of inflammatory bowel disease (Kappaproct®, Index Pharmaceutical AB, Solna, Sweden). SEQ ID NO 10 (IDX0980) was originally used, as it is known to be a strong immunomodulatory olignucleotide in human (Kerkmann et al., 2005; Wikström et al., 2007).

The present inventors make available an isolated and substantially purified oligonucleotide chosen among SEQ ID NO 1-8.

According to one embodiment, at least one nucleotide in such oligonucleotides has a phosphate backbone modification. Preferably said phosphate backbone modification is a phosphorothioate or phosphorodithioate modification.

The inventors also make available pharmaceutical compositions comprising an oligonucleotide according to any one of SEQ ID NO 1-8. Said pharmaceutical compositions further preferably comprise a pharmacologically compatible and physiologically acceptable excipient or carrier, chosen from saline, liposomes, surfactants, mucoadhesive compounds, enzyme inhibitors, bile salts, absorption enhancers, cyclodextrins, or a combination thereof.

Another embodiment of the invention is the use of an isolated and substantially purified oligonucleotide according to any one of SEQ ID NO 1-8 for the manufacture of a pharmaceutical composition for the treatment, and/or alleviation of multiple sclerosis.

Another embodiment is the use of an isolated and substantially purified oligonucleotide according to SEQ ID NO 9 [IDX0150] or SEQ ID NO 10 [IDX0980] for the manufacture of a pharmaceutical composition for the treatment, and/or alleviation of multiple sclerosis, in particular relapsing-remitting multiple sclerosis.

Without wishing to be bound to any specific theory, the inventors contemplate that the effect of the inventive compounds at least in part is accountable to their capability to inhibit or reduce the influx of autoaggressive cells to the central nervous system by down-regulating the expression of at least one cell surface marker. Consequently, one embodiment of the invention involves the administration of an oligonucleotide according to SEQ ID NO 1-8 or 9-10 in an amount effective to inhibit or reduce the influx of autoaggressive cells to the central nervous system by down-regulating the expression of at least one cell surface marker.

It is contemplated that the oligonucleotides and the methods of their use is also generally applicable to the treatment or alleviation of an inflammatory disease of the central nervous system wherein said oligonucleotide is administered in an amount effective to inhibit or reduce the influx of mononuclear cells to the central nervous system by down-regulating the expression of at least one cell surface marker.

Preferably said at least one cell surface marker is chosen among CD49d, CXCR3 (CD183), CCR2 (CD192), and CCR5 (CD195). According to one embodiment, said oligonucleotide is chosen among SEQ ID NO 1 [IDX9045], SEQ ID NO 2; [IDX9054]; SEQ ID NO 7 [IDX9058); SEQ ID NO 3 [IDX9038]. Preferably said oligonucleotide is SEQ ID NO 1 [IDX9045]. According to another embodiment, said at least one cell surface marker is CD49d and the oligonucleotide is chosen from SEQ ID NO 3 [IDX9038] or SEQ ID NO 7 [IDX9058].

The inventors however also contemplate, again without wishing to be bound to a specific theory, that the effect is at least in part accountable to the inhibition or reduction of the influx of autoaggressive cells to the central nervous system by reducing the production of VEGF.

Consequently, according to another embodiment of the invention, the oligonucleotide is chosen among SEQ ID NO 1 [IDX9045] and SEQ ID NO 10 [IDX0980].

The invention also makes available a method for the treatment, and/or alleviation of multiple sclerosis, wherein an oligonucleotide is administered in an amount effective to inhibit or reduce the influx of autoaggressive cells to the central nervous system by down-regulating the expression of specific cell surface markers.

Preferably a pharmaceutical composition comprising an oligonucleotide according to any one of SEQ ID NO 1-8, 9 and 10 is administered to a patient.

Preferably, the route of administration is chosen from mucosal, subcutaneous, intramuscular, intravenous and intraperitoneal administration. Preferably the mucosal administration is chosen from nasal, oral, gastric, ocular, rectal, urogenital and vaginal administration.

In the above method, the cell surface marker is at least one of CD49d, CXCR3 (CD183), CCR2 (CD192), and CCR5 (CD195), and the oligonucleotide is chosen among SEQ ID NO 1 [IDX9045], SEQ ID NO 2; [IDX9054]; SEQ ID NO 7 [IDX9058); SEQ ID NO 3 [IDX9038].

According to a preferred embodiment, the cell surface marker is CD49d and the oligonucleotide is chosen from SEQ ID NO 3 [IDX9038] or SEQ ID NO 7 [IDX9058].

According to another embodiment of a method for the treatment, and/or alleviation of multiple sclerosis, said oligonucleotide is administered in an amount effective to inhibit or reduce the influx of autoaggressive cells to the central nervous system by reducing the production of VEGF. In this embodiment, the oligonucleotide is preferably chosen among SEQ ID NO 1 [IDX9045] and SEQ ID NO 10 [IDX0980].

According to an embodiment, the oligonucleotide is administered in an amount of about 1 to about 2000 μg per kg body weight, preferably about 1 to about 1000 μg per kg body weight. Most preferably the oligonucleotide is administered in an amount of about 1 to 500 μg per kg body weight.

In a method according to the invention, the route of administration is chosen from mucosal, subcutaneous, intramuscular, intravenous and intraperitoneal administration. According to an embodiment of the method, the mucosal administration is chosen from nasal, oral, gastric, ocular, rectal, urogenital and vaginal administration.

Nasal administration constitutes one embodiment of the method according to the invention. There are several methods and devices available for nasal administration; single or multi-dosing of both liquid and powder formulations, with either topical or systemic action. Using appropriate devices or administration techniques, it is possible to target the olfactory bulb region for delivery to the CNS. The present invention is not limited to particular methods or devices for administering the oligonucleotides to the nasal mucous membrane. The initial animal studies have shown that simple instillation by pipette works satisfactorily, although for human use, devices for reliable single or multi dose of administration would be preferred.

According to another embodiment of the invention, the oligonucleotides are administered to the mucous membrane of the colon through rectal instillation, e.g. in the form of an aqueous enema comprising the oligonucleotides suspended in a suitable buffer.

According to another embodiment of the invention, the oligonucleotides are administered to the mucous membrane of the lungs or the airways through inhalation of an aerosol, comprising the oligonucleotides suspended in a suitable buffer, or by performing a lavage, also comprising the oligonucleotides suspended in a suitable buffer.

According to yet another embodiment of the invention, the oligonucleotides are administered to the mucous membrane of the urogenital tract, such as the urethra, the vagina etc through application of a solution, a buffer, a gel, salve, paste or the like, comprising the oligonucleotides suspended in a suitable vehicle.

A particular embodiment involves the use of an oligonucleotide according to the invention for use in conjunction with the administration of Tysabri, an antibody directed to CD49d, a cell surface marker on T-cells. There are indications that the oligonucleotides according to the invention can down regulate CD49d, which might reduce transmigration of T-cells through the blood-brain barrier. The inventors thus make available a combination therapy involving the use of oligonucleotide compounds together with an anti-CD49d antibody. This is contemplated to be able to reduce antibody consumption, and thereby reduce the cost, side-effects and risks associated with the said antibody therapy. Consequently, in this embodiment, said compound is administered sufficiently before the administration of an antibody in order to allow the down-regulation of the specific cell surface molecules towards which the antibody is directed.

A skilled person is well aware of the fact that there are several approaches to the treatment of MS. Naturally new approaches are constantly being developed, and it is conceived that the oligonucleotides, their use and methods of treatment according to the present invention, will find utility also in combination with future treatments. The inventors presently believe that the inventive oligonucleotides, their use and methods of treatment would be useful as a stand-alone therapy for MS. It cannot however be excluded that the inventive oligonucleotides will have utility in combination with existing or future anti-MS treatments.

The oligonucleotide is administered in a therapeutically effective dose. The definition of a "therapeutically effective dose" is dependent on the disease and treatment setting, a "therapeutically effective dose" being a dose which alone or in combination with other treatments results in a measurable improvement of the patient's condition. A skilled person can determine a therapeutically effective dose either empirically, or based on laboratory experiments, performed without undue burden. The treating physician can also determine a suitable dose, based on his/her experience and considering the nature and severity of the disease, as well as the patient's condition.

Another embodiment is the administration of the oligonucleotide in two or three or more separate doses, separated in time by about 12, about 24 hours.

The invention finds utility in the treatment of MS, as supported by the in vivo and in vitro data presented in the experimental section and illustrated in the attached figures.

The embodiments of the invention have many advantages. So far, the administration of an oligonucleotide in the doses defined by the inventors has not elicited any noticeable side-effects. Further, the mucosal administration is easy, fast, and painless, and surprisingly results in a systemic effect. It is held that this effect, either alone, or in combination with existing and future anti-MS treatments, offers a promising approach to fight this disease as well as related diseases.

EXAMPLES

Example 1

The Effect of Oligonucleotides on Rat Splenocytes

The present inventors set out to find and validate candidate compounds that would be beneficial for the treatment and/or alleviation of MS. The compounds used in these studies are based on oligodeoxynucleotides. Before specific oligonucleotides could be tested for their beneficial effect in in vitro and in vivo studies, an assay was developed which enabled the inventors to test whether an oligonucleotide has an immunomodulatory effect in rat. For this purpose, the inventors used a rat splenocyte-based assay, where splenocytes were incubated for a specified time with a selection of inventive compounds. After the incubation, mRNA expression for several immunological relevant markers was analyzed (IFN-alpha, IFN-beta, IFN-gamma, IL-6, IL-10, TNF-alpha, VEGF-A, CCL-2, CCL-3, CCL-4, CCL-5, CXCL-1, CXCL-2, CXCL-10 and TGF-beta1), which served as a base to identify compounds that are showing immunomodulatory effects in rat and enabled the selection of compounds to be used in further rat studies.

Materials and Methods

Oligodeoxynucleotides: In the present study, 6 different oligonucleotides were used for stimulation experiments using rat derived splenocytes. All oligonucleotides were synthesized by Biomers.net (Ulm, Germany). Upon arrival, all oligonucleotide were diluted with sterile water in a series of different dilutions. The optical density (OD) A260/280 was determined in at least five or more samples of each dilution using a spectrophotometer (SmartSpec™ 3000, Biorad, Hercules, Calif.). The average concentration of all readings, for all dilutions, was calculated in order to determine the concentration of the stock. These stock solutions were all stored at $-20°$ C. The different working solutions used in the experiments: 1 µM and 10 µM were prepared by diluting the oligonucleotide stock solutions further in distilled water (Invitrogen, Carlsbad, Calif.). Repeated thawing/freezing cycles were minimized to limit any degradation of the compounds.

PCR primers: Gene-specific primers were designed by using Applied Biosystems Primer Express software (Table 2; Foster City, Calif.). Amplification/detection of contaminating genomic DNA was avoided by constructing one of the primers over an exon/intron boundary. Primer oligonucleotides were ordered from MWG Biotech (Ebersberg, Germany).

Rat splenocyte preparation: Six spleens derived from female DA rats were used in the study. The spleens were not pooled but dealt with individually to assess the degree of variability. Cell suspensions were prepared under sterile conditions by using a 70 µm nylon cell strainer (Becton Dickinson, Franklin Lakes, N.J., USA). Cells were then washed twice in complete RPMI 1640 (RPMI 1640 containing 5% heat inactivated FCS (Invitrogen), 2 mM L-glutamine (Sigma-Aldrich), 100 U/ml penicillin and 100 µg/ml streptomycin (Invitrogen) at 1200 rpm for 7-10 minutes at 4° C. The supernatant was decanted and cells were resuspended in 1 ml red blood cell lysing buffer (Sigma-Aldrich) and incubated further for two minutes at room temperature. Another 5 ml of complete medium was added before centrifugation, which was performed as previously described. After decanting the supernatant, the pellet was resuspended in complete medium and cell numbers were determined with 0.4% Trypan blue exclusion (Sigma-Aldrich) using a Nikon Eclipse TE2000-S microscope (Nikon, Tokyo, Japan).

In vitro stimulation: Cells were plated out in a 96-well V-bottom plate in complete RPMI 1640 medium at a concentration of $10 \times 10^6$ cells/ml, corresponding to $5 \times 10^5$ cells per well. Directly after plating the cells, an oligonucleotide diluted in RPMI 1640 medium were added so that the final concentration of the added oligonucleotide reached 1 µM and 10 µM respectively. Incubations were performed in duplicates. Cells were incubated in a humidified cell culture incubator (Thermo Scientific, Waltham, Mass.) with 5% $CO_2$ in air at 37° C. for 24 hours. After the incubation period cell suspensions were pooled and added to 1 ml ice cold PBS and thereafter washed at 1200 rpm for 10 minutes at 4° C. Finally supernatant was removed and the cell pellet subsequently dissolved and lysed in 350 µl RLT buffer with 1% of R-mercaptoethanol added. The lysed cell suspensions were frozen at −20° C. until further processing.

RT-PCR: Total RNA was extracted (Qiagen total RNA extraction kit, Qiagen, Hilden, Germany). Samples were incubated with 27 kU of DNase for 30 minutes at 37° C. in order to avoid amplification/detection of contaminating genomic DNA. After the RNA was eluted in 40 µl RNase-free water, 5 µl of RNA eluate was taken for determination of the RNA concentration by spectrophotometry. Reverse transcription was performed with 0.15-1 µg of total RNA, random hexamers (0.1 µg; Invitrogen), and superscript reverse transcriptase (200 U; Invitrogen) following manufacturers guidelines. The resulting cDNA was diluted with sterile deionised water to form cDNA stock solutions. Amplification was performed using the Applied Biosystems 7500 Real time PCR System using SYBR-Green I (Applied Biosystems) with a two-step PCR protocol (95° C. for 10 minutes, followed by 40 cycles of 95° C. for 15 seconds and 60° C. for 1 minute). In preliminary experiments, the primer pairs had been tested using a conventional PCR protocol. The PCR products were run in an agarose gel and were in all cases confined to a single band of the expected size. All primers used are listed in Table 2.

Semi-quantitative assessment of mRNA levels was performed using the ΔΔCt method with amplification of mRNA and actin-gamma, a house-keeping gene, in separate tubes. All samples were run in duplicates. Real-time PCR data (individual ΔCt and RQ values) were calculated and analysed with 7500 Real time PCR System SDS Software. The individual values were then exported to Excel. For each particular gene the average RQ values from the duplicate samples were normalised against the average RQ value of the samples that were stimulated with medium only. The mean values and standard deviation of the six individual splenocyte populations were calculated accordingly.

TABLE 2

Realtime PCR primer sequences

| Gene | | Oligonucleotide sequence |
|---|---|---|
| IFN-alpha | Forward | 5'-CCTCTTCACATCAAAGGAGTCATCT |
| | Reverse | 5'-ACAGGCTTGCAGACCACTCA |
| IFN-beta | Forward | 5'-GCGTTCCTGCTGTGCTTCTC |
| | Reverse | 5'-TGCTAGTGCTTTGTCGGAACTG |
| IFN-gamma | Forward | 5'-TCGCCAAGTTCGAGGTGAA |
| | Reverse | 5'-TAGATTCTGGTGACAGCTGGTGAA |
| IL-6 | Forward | 5'-CACCCACAACAGACCAGTATATACCA |
| | Reverse | 5'-TGCCATTGCACAACTCTTTTCT |
| IL-10 | Forward | 5'-TGCGACGCTGTCATCGAT |
| | Reverse | 5'-GACACCTTTGTCTTGGAGCTTATTAA |
| TNF-alpha | Forward | 5'-TGATCGGTCCCAACAAGGA |
| | Reverse | 5'-TGCTTGGTGGTTTGCTACGA |
| CXCL-1 | Forward | 5'-TCACTTCAAGAACATCCAGAGTTTG |
| | Reverse | 5'-GTGGCTATGACTTCGGTTTGG |
| CXCL-2 | Forward | 5'-AAGATACTGAACAAAGGCAAGGCTAA |
| | Reverse | 5'-TTGATTCTGCCCGTTGAGGTA |

TABLE 2-continued

Realtime PCR primer sequences

| Gene | | Oligonucleotide sequence |
|---|---|---|
| CXCL-10 | Forward | 5'-CATGTTGAGATCATTGCCACAA |
| | Reverse | 3'-CCGCTTTCAATAAGCTCTTGATG |
| CCL-2 | Forward | 5'-CCAATGAGTCGGCTGGAGAA |
| | Reverse | 3'-GAGCTTGGTGACAAATACTACAGCTT |
| CCL-3 | Forward | 5'-AGCCGGGTGTCATTTTCCT |
| | Reverse | 3'-TTGGACCCAGGTCTCTTTGG |
| CCL-4 | Forward | 5'-GCACCAATAGGCTCTGACCCT |
| | Reverse | 3'-TTGGTCAGAAATACCACAGCTGG |
| CCL-5 | Forward | 5'-CCTTGCAGTCGTCTTTGTCACT |
| | Reverse | 3'-GATGTATTCTTGAACCCACTTCTTCTC |
| VEGF-A | Forward | 5'-GGGCTGCTGCAATGATGAA |
| | Reverse | 3'-TTGATCCGCATGATCTGCAT |
| TGF-beta1 | Forward | 5'-ACGTGGAAATCAATGGGATCA |
| | Reverse | 3'-GGAAGGGTCGGTTCATGTCA |
| | Reverse | 5'-CCGACGATGGAAGGAAACAC |

Results

Initially, the focus of the study was on the cytokines IFN-alpha, IFN-beta and IL-10, due to their suggested protective effects in MS and therefore graphs for only these factors are included.

Both IFN-alpha (FIG. 1) and IFN-beta mRNA (FIG. 2) were induced by several oligonucleotides and especially IDX9052, IDX9054, IDX9060 and IDX0980 induced high levels of mRNA for these genes. Oligonucleotides that were not capable of inducing IFN-alpha/beta include IDX9022 and IDX9045.

In contrast to the type 1 interferons, IL-10, a potent Th-2 related cytokine was induced at much lower levels. IDX9060 and IDX0980 are among the oligonucleotides that induce the highest levels of IL-10 as shown in FIG. 3. Values were normalized to the mean RQ value of the samples that were stimulated with medium only. Data are shown as means±SD of splenocytes derived from 6 spleens.

The patterns of IFN-gamma, CXCL-10 and VEGF-A were nearly similar compared to the pattern of the type I interferons and were moderately to strongly induced by several oligonucleotides (data not shown). Most oligonucleotides induced only limited amounts of IL-6 mRNA and the difference between the tested compounds was relatively small (data not shown).

TNF-alpha and TGF-beta mRNA were hardly affected by any of the tested oligonucleotides as none of these molecules could change its expression significantly. Interestingly, however was the observation that IDX9022 and IDX9045 gave a conspicuous down regulation of TGF-beta (data not shown).

If one attempts to summarize the data on the remaining chemokines, then it becomes clear that there are two groups: one group consisting of genes that respond upon treatment with an oligonucleotide and one group consisting of genes that do not respond or even show a down-regulation after culture with an oligonucleotide. To the first group belong MIP-1alpha, MCP1 and CCL-5, whereas CCL-4, MIP-2 and CINC belong to the latter group. In neither of the groups a clear overlap between the genes could be observed.

In conclusion, it has become evident that the inventors' candidate drugs are able to stimulate rat cells and thereby change expression levels of several immunological relevant marker genes. These results provided the basis for focusing on specific oligonucleotides in further studies, including in a rat EAE model.

Example 2

Reduction of CD49d Expression on Rat Cells In Vitro

The inventors set out to investigate if the inventive compounds can reduce CD49d (an important molecule on surface of lymphocytes that interacts with receptors on endothelial cells) and thereby reducing the transmigration of the cells into the CNS, i.e. a critical step in MS pathogenesis. The inventors used splenocytes or blood from rat for studying expression of CD49d upon stimulation with the inventive compounds.

Material and Methods

Splenocytes (n=3) or PBMC (n=1) from DA rats were incubated at 37° C. in a volume of 500 µl of complete RPMI-medium (containing 10% FCS, 1% PenStrep, 2 mM L-glutamine, 10 mM HEPES and 1 mM Sodium Pyruvate) in 48-well plates at a concentration of $2 \times 10^6$ cells/ml and treated with 10 µM of IDX9022, IDX9058, IDX9038, IDX0150, IDX9054 and IDX9045.

After 48 hours, 200 µl of the cell suspension was spun down in 96-well plates, resuspended in 100 µl of 2% FCS (in PBS) and incubated with fluorochrome conjugated anti-CD3 and anti-CD49d antibodies (Becton Dickinson, San Jose, Calif.) for 30 min at 4° C. The cells were then washed twice in pure PBS and subsequently analyzed by FACS using a FACSArray bioanalyzer (BD) for surface antigen expression analysis.

Results

Splenocytes from 3 pooled DA rats showed down-regulation of CD49d upon treatment with inventive compounds (FIG. 4). This down-regulation was most pronounced with IDX0150, IDX9045 and IDX9054, 48 h after incubation. PBMC from 1 DA rat showed down-regulation of CD49d upon treatment with inventive compounds (FIG. 5). This down-regulation was most pronounced with IDX0150 and IDX9038, 48 h after incubation.

A decrease in CD49d expression was observed in splenocytes and PBMC treated with the inventive compounds. These properties of the inventive compounds could reduce the process of transmigration and there by influx of cells into CNS, either as stand alone or as a combinatory treatment with antibody therapy.

Example 3

Animal Studies

The inventors commissioned animal studies to confirm their hypothesis and to test different candidate compounds. Two studies were performed with MOG-induced Experimental Autoimmune Encephalomyelitis (EAE) in DA rats.

MOG-induced EAE in DA rats is a well characterised experimental model with high reproducibility sharing many features with its human counterpart multiple sclerosis, and as such is an appropriate model for therapeutic testing (Gold et al., 2006, Friese et al., 2006). Following immunization with MOG in IFA, animals become progressively paralysed from the tail, through the back legs to the front legs due to progressive degeneration of myelin caused by infiltrating inflammatory immune cells into the spinal cord and brain. Pathogenesis is chronic relapsing, with animals partially recovering and then relapsing with heightened disease, and is a result of both monocytes and T cell (type 1 cytokines) and B cell (antibody) activities.

The rat was chosen as a rodent species since it is a widely accepted relapsing/remitting experimental model. The selected strain has documented susceptibility to CNS inflammation. In general, 50-80% of immunized rats develop relapsing disease after a titrated immunization. The remaining ones develop either late chronic disease or die during the first attack.

Test animals: DA-rats (female, 180-250 g, 10-14 weeks of age) from B & K, Sollentuna, Sweden were used. The animals were allowed to acclimatize for at least 7 days before test starting. In this period the animals were observed daily to ascertain their fitness for the study. Animals showing signs of ill-health, any abnormalities or bodyweight range extremes were replaced before the study.

The groups were distributed within and between barriers in a manner which allowed equalisation of environmental influences across the study. The test animals were identified by an ear tag. The cage card stated number of the experiment, and the group code alone.

Housing: The animals were housed four per cage, unless reduced by mortality or isolation. The cages were conventional makrolon plastic cages with stainless steel lids. Aspen chips were used as flooring material. Filtered, not recirculated air was supplied. The temperature was maintained within the range 20-23° C. and the relative humidity within the range 40-60%. Both temperature and relative humidity were monitored daily. Lighting conditions were 12 hours light and 12 hours dark (07.00-19.00).

Diet: The test animals were given conventional rodent diet (R 36 (irradiated) from Lactamin, Sweden) ad lib. Before delivery, each batch of diet was analyzed by the supplier for various nutritional components and chemical and microbiological contaminants. The suppliers' analytical certificates were scrutinized and approved before any batch of diet was released for use.

This diet contained no added antibiotic or other chemotherapeutic or prophylactic agent. The test animals were given water ad lib (municipal drinking water) via polyethylene or polycarbonate pipes with sipper tubes.

Immunization procedure: The rats were immunized (day=0) by injecting i.d. in the base of the tail 0.1 ml of an emulsion composed of 30 µg rat MOG pH3 (5.2 mg/ml stock) in Incomplete Freund's Adjuvant (Sigma, St. Louis, USA). This procedure is known to result, starting approximately from day 10, in the appearance of a progressive paralysis, arising from the tail and progressively ascending up to the forelimbs.

Duration of treatment: The test compounds and control were administered twice before (i.e. day 11 and day 15) the peak of the first attack, and the third treatment at day 20 (during the peak of the first attack).

Test substances: In the first study, two proprietary oligonucleotides were used, IDX9052 (SEQ ID NO 5) and IDX9054 (SEQ ID NO 2), together with a publicly available oligonucleotide, IDX0980 (SEQ ID NO 10). In the second study, one proprietary oligonucleotide was used; IDX9054 (SEQ ID NO 2). The sequence of the test substances is given in Table 1.

The test compounds in the first study (IDX9052, IDX9054 and IDX0980) were administered s.c. in a total volume of 100 µl in the neck. This dose was administered three times. The test compound in the second study (IDX9054) was administered s.c in a total volume of 100 µl in the neck or i.n in a total volume of 40 µl on the nose. The drugs were administered three times either s.c or i.n. In both studies, PBS was used as both vehicle and control (blank). The dose administered was 150 µg per immunization in all studies.

Study design: The first study involved four groups of 12 animals each. All the groups were immunized with rat MOG in IFA, according to the immunization protocol. All compounds were immunized three times.

Group 1: control group: vehicle alone PBS by s.c. route
Group 2: dosed with 150 µg of IDX9052 by s.c. route
Group 3: dosed with 150 µg of IDX9054 by s.c. route
Group 4: dosed with 150 µg of IDX0980 by s.c. route The number of animals per group was the minimum number allowing an accurate assessment of observed pharmacological effects.

The second study involved three groups of 16 animals each. All the groups were immunized with rat MOG in IFA, according to the immunization protocol. All compounds were immunized three times.

Group 1: dosed with 150 µg of IDX9054 by s.c route
Group 2: control group: vehicle alone PBS by i.n. route
Group 3: dosed with 150 µg of IDX9054 by i.n route Clinical observations: The animals were visually inspected at least twice daily for evidence of reaction to treatment or ill-health. Starting from day 5 the animals were examined individually for the presence of paralysis by means of a clinical score as follows:

0=no sign of disease
1=tail weakness or tail paralysis
2=hind leg paraparesis or hemiparesis
3=hind leg paralysis or hemiparalysis
4=complete paralysis (tetraparaplegy)
5=moribund state or death Ataxia was routinely assessed. A disease remission was defined as an improvement in disease score for at least 2 days consecutively. A relapse was defined as an increase in the clinical deficit of at least 2 points that lasted for at least 2 days.

The results of the clinical scores were expressed as the mean (±SEM) score within each group. The effects of the test substances were compared with that of the vehicle-treated control group. Differences of clinical score values among groups were analyzed by Kruskal-Wallis test followed, in case of significance, by the pair wise Wilcoxon test, at each measurement time.

Observation of the animals took place in a quiet room. Clinical signs were monitored daily in each group of treatment in a blind fashion by a technician who was unaware of the treatments. The body weight of the animals was also monitored daily.

Animals considered to be in pain, distress or in moribund condition were examined by the staff veterinarian or authorized personnel and, if necessary, humanely sacrificed to minimize undue pain or suffering.

Results

Animal status: In the first study all animals tolerated s.c treatment with vehicle or IDX9052, IDX9054 and IDX0980 without any adverse behavioral or physical effects as assessed daily. In the second study, all animals tolerated i.n and s.c. treatment with vehicle or IDX9054 without any adverse behavioral or physical effects as assessed daily, except from one animal in the PBS i.n control group that died immediately following a treatment, an event not considered to be natural. One animal in the same group developed arthritis and was scarified according to ethical guidelines.

At disease debut there was the usual associated drop in weight which continued thereafter in all studies. Due to the variable disease incidence and mortality between groups, statistical analysis of differences between groups is not informative. However, both IDX9054 and IDX0980-treated groups lost less weight than PBS control group in the first study and in the second study IDX9054 i.n and s.c-treated groups lost less weight than PBS i.n control group.

Clinical disease course: In study number one all rat groups were assessed daily for clinical signs of disease. They began to develop EAE from day 10 (FIG. 6). Four animals in the IDX0980 treated group and three animals in the IDX9054 treated groups never developed disease, but otherwise all other groups reached 100% clinical disease incidence by day 16 (FIG. 7). There was a significant difference between incidence in the IDX0980 treated group and the control group (p=0.0285). All animals are included in the presented analysis. In the second study, rats began to develop EAE from day 11 (FIG. 8). Five animals in both the s.c and i.n IDX9054 treated groups never developed disease, but the PBS i.n group reached 100% clinical disease incidence by day 26. There was a significant difference between incidence in the IDX9054 s.c and i.n-treated groups compared to the i.n control group (p=0.02).

Disease course developed with a relapsing-remitting course which progressively worsened over time. As not all animals in a group developed disease at exactly the same time, and their disease courses were thus not completely in-phase with each other, the standard deviations of the mean values presented are variable (Not shown).

In the first study, there was a significant difference in onset of EAE in the IDX9054 treated group (p=0.0318), being slightly delayed compared to the control group. While there was no statistically significant difference in either mean disease severity, cumulative score or mean maximum score between groups, there was a definite tendency that both IDX0980- and IDX9054-treated groups had reduced weight loss, reduced disease severity and lower mortality rates than both other groups (FIG. 9). In the second study, there was no statistically significant difference in either onset of EAE mean disease severity, cumulative score or mean maximum score between groups, but there was a definite tendency that both i.n- and s.c-IDX9054-treated groups had reduced weight loss, reduced disease severity and lower mortality rates than the control PBS i.n group. The cumulative score and mean maximal score for the i.n-IDX9054-treated group was marginally less than in the s.c-IDX9054-treated group.

This MOG-EAE model is a severe disease model, and rats either died or were sacrificed due to ethical regulations in each group, being assigned a maximum score of 5 or 4, respectively, thereafter in all presented analyses. The mortality was generally high, but reflects the natural variation we routinely experience in the model.

A summary of all clinical data is presented in Tables 3-4, and a summary of the statistical analysis is presented below each table.

TABLE 3

Summary of pre-clinical data from the first EAE study

| GROUP | n | Incidence (%) | Cumulative Score | Mean cumulative Score (SD) | Mortality % (no./total) | Mean Weight Change gram |
|---|---|---|---|---|---|---|
| 0980 s.c | 12 | 67 | 543 | 45 (37) | 50.0 (6/12) | +8.25 |
| 9054 s.c | 12 | 75 | 604 | 50 (38) | 58.3 (7/12) | +3.88 |
| PBS s.c | 12 | 100 | 793 | 66 (24) | 66.6 (8/12) | −2.67 |
| 9052 s.c | 12 | 100 | 762 | 64 (24) | 66.6 (8/12) | −4.16 |

P-Values for Pre-Clinical Study Number One
IDX0980 vs PBS
CUMULATIVE SCORE p=0.2128
MAX SCORE p=0.2444
DISEASE DURATION p=0.3008
DAY OF ONSET p=0.2873
INCIDENCE p=0.0285*
IDX9054 vs PBS
CUMULATIVE SCORE p=0.3548
MAX SCORE p=0.4490
DISEASE DURATION p=0.1018
DAY OF ONSET p=0.0318*
INCIDENCE p=0.0641
IDX9052 vs PBS
CUMULATIVE SCORE p=0.6858
MAX SCORE p=0.6806
DISEASE DURATION p=0.3907
DAY OF ONSET p=0.6123
INCIDENCE p=−(both 100%)

TABLE 4

Summary of pre-clinical data from the second EAE study

| GROUP | n | Incidence (%) | Cumulative Score | Mean cumulative Score (SD) | Mortality % (no./total) | Mean Weight Change gram |
|---|---|---|---|---|---|---|
| PBS i.n | 16 | 100 | 867 | 62 (25) | 50.0 (7/14) | −8.71 |
| IDX-9054 i.n | 16 | 68 | 672 | 42 (39) | 21 (5/16) | +11.44 |
| IDX-9054 s.c | 16 | 68 | 726 | 45 (39) | 21 (5/16) | +6.3 |

P-Values for Pre-Clinical Study Number Two
IDX9054 i.n vs PBS i.n
CUMULATIVE SCORE p=0.20
MAX SCORE p=0.055
DISEASE DURATION p=0.29
DAY OF ONSET p=0.17
INCIDENCE p=0.02*
IDX9054 s.c vs PBS i.n
CUMULATIVE SCORE p=0.21
MAX SCORE p=0.12
DISEASE DURATION p=0.24
DAY OF ONSET p=0.16
INCIDENCE p=0.02*

MOG-induced EAE in DA rats is a well characterized experimental model with high reproducibility. It shares many features with its human counterpart multiple sclerosis, and as such is an appropriate model for therapeutic testing (Gold et al., 2006, Friese et al., 2006).

Following immunization with MOG in IFA, animals become progressively paralyzed from the tail, through the back legs to the front legs due to progressive degeneration of myelin caused by infiltrating inflammatory immune cells into the spinal cord and brain. Pathogenesis is chronic relapsing, with animals partially recovering and then relapsing with heightened disease, and is a result of both monocytes and T cell (type 1 cytokines) and B cell (antibody) activities.

The test substances are oligonucleotides with proven immunostimulatory activity in vitro. Their specific immunostimulatory profile differs depending on the sequence of the oligonucleotide, which makes comparative analyses of their effects in vivo on ongoing inflammatory responses of therapeutic interest. The purpose of the two EAE-animal studies was to investigate the effect of IDX9052, IDX9054 and IDX0980 in a model of relapsing/remitting MOG-induced EAE in DA rats.

Treatment with all test oligonucleotides, or with vehicle alone, did not cause any adverse physiological or behavioral effects in recipient rats. Treatment was initiated at just prior to the first bout of disease, in order to have first allowed disease to develop normally but then to dampen the ongoing proinflammatory cascade. Additional administrations were timed to coincide with height of disease and start of the clinical disease phase. Recovery from this first period of EAE was more pronounced in both IDX0980- and IDX9054-treated groups, and development of subsequent clinical bouts was less pronounced in the IDX0980-treated group. All measured parameters were reduced in both IDX0980- and IDX9054-treated groups compared to vehicle-treated groups.

SEQ ID NO 5 (IDX9052) was a strong inducer of IFN alpha/beta in rat splenocytes but showed no reduced severity of disease in the EAE rat model. Thus, the reduced severity of disease observed in the EAE rat model upon treatment with IDX9054 and IDX0980 can not be correlated to only IFN beta production. Furthermore, the results obtained with SEQ ID NO 2 (IDX9054) indicate that this compound has a therapeutic effect, both s.c. and i.n. in MOG-EAE in DA rats.

Example 4

Reduction of CD49d In Vitro in Patient Samples

To investigate if the inventive compounds can reduce CD49d expression the inventors used PBMC isolated from RRMS patients for studying expression of CD49d upon stimulation with candidate compounds.

Material and Methods

PBMC from RRMS patients (n=9) was obtained from BD CPT vacutainer (Becton Dickinson). The cells were immediately incubated at 37° C. in a volume of 500 µl of complete RPMI-medium (containing 10% FCS, 1% PenStrep, 2 mM L-glutamine, 10 mM HEPES and 1 mM Sodium Pyruvate) in 48-well plates at a concentration of $2\times10^6$ cells/ml and treated with 1, 10 and 25 µM of each of the oligonucleotide compounds (Table 1). Cells incubated with oligonucleotides were harvested after 48 h, washed in PBS and re-suspended in PBS supplemented with 2% FCS. The cells were stained with two different sets of fluorochrome conjugated antibody mixtures; (1) anti-CD3 APC, anti-CD49d PE and (2) anti-CD19 PE Cy7, anti-CD49d APC for 30 min at 4° C. The antibodies were purchased from Becton Dickinson. After staining, the cells were washed in PBS and subsequently analyzed by FACS using a FACSArray bioanalyzer (Becton Dickinson).
Results PBMC isolated from RRMS patients showed down-regulation of CD49d on T cells in a dose dependent manner upon stimulation with the oligonucleotides (FIG. 10).

A decrease in CD49d expression on cells was observed in PBMC isolated from RRMS patients treated with the inventive compounds. These properties of the inventive compounds could reduce the transmigration and thereby the influx of cells into CNS.

Example 5

Reduction of Chemokine Receptors In Vitro in Patient Samples

The influx of blood mononuclear cells (e.g. T-cells, B-cells, monocytes) in CNS plays a crucial role in the pathogenesis of MS. Blocking or reducing the influx would therefore be beneficial for the treatment of MS. Chemokine receptors like CCR5 (CD195), CCR2 (CD192), and CXCR3 (CD183) are expressed on mononuclear cells and are involved in recruitment of the cells to the site of inflammation. To investigate if the inventive compounds can reduce expression of said chemokine receptors, the inventors stimulated PBMC isolated from RRMS patients with the inventive compounds.

Material and Methods

PBMCs from RRMS patients (n=3) were isolated using BD CPT vacutainer. The cells were immediately incubated at 37° C. in a volume of 500 µl of complete RPMI-medium (containing 10% FCS, 1% PenStrep, 2 mM L-glutamine, 10 mM HEPES and 1 mM Sodium Pyruvate) in 48-well plates at a concentration of $2\times10^6$ cells/ml and treated with 1, 10 and 25 µM of each inventive compounds. Cells incubated with the oligonucleotides were harvested after 48 h, washed in PBS and re-suspended in PBS supplemented with 2% FCS. The cells were stained with three different sets of fluorochrome conjugated antibody mixtures; (1) anti-CD3 PE-Cy-7, anti-CCR5 APC-Cy7, anti-CCR2 Alexa Fluor 647, anti-CXCR3-PE, (2) anti-CD19 PE-Cy-7, anti-CCR5 APC-Cy7, anti-CCR2 Alexa Fluor 647, anti-CXCR3 PE and (3) anti-CD14 PE-Cy-7, anti-CCR5 APC-Cy7, anti-CCR2 Alexa Fluor 647, anti-CXCR3 PE, for 30 min at 4° C. The antibodies were purchased from Becton Dickinson. After washing in PBS, the cells were analyzed using a FACSarray flow cytometer (Becton Dickinson).

Results

PBMC isolated from RRMS patients (n=3) showed down-regulation of CXCR3 on T cells (CD3 positive) after stimulation with inventive compounds, especially by IDX9045 (FIG. 11). CCR5 was also down-regulated on T cells after oligonucleotide treatment, especially by IDX9022 (data not shown).

PBMC isolated from RRMS patients (n=3) showed down-regulation of CXCR3 on CD19 positive cells. The oligonucleotides that showed the most potent down-regulatory effect of this receptor were IDX9038, IDX9054, IDX9058, IDX9045, IDX9004, and IDX0980 (FIG. 12).

PBMC isolated from RRMS patients (n=3) showed down-regulation of CXCR3, CCR5 and CCR2 on CD14 positive cells. The oligonucleotides showing the most potent down-regulatory effect of CXCR3, CCR5 and CCR2 are shown in FIGS. 13, 14 and 15 A and B, respectively.

A decrease in chemokine receptor (CCR5, CXCR3, CCR2) expression on T, B and monocytes was observed in PBMC isolated from RRMS patients treated with the inventive compounds. These properties of the inventive compounds could play important role in reduction of the migration of these cells towards the CNS.

Example 6

Reduction of Chemotaxis of Leukocytes Isolated from RRMS Patients

MCP-1 and RANTES are potent chemokines for the recruitment of blood mononuclear cells, in particular monocytes, T-cells, and B-cells to the site of inflammation. Chemotaxis of blood mononuclear cells towards MCP-1 and RANTES is mediated mainly through CCR2, and CCR5 receptors, respectively. The aim of this study was to demonstrate that the decreased expression of CCR2, and CCR5 by inventive compounds as shown in example 5, can indeed reduce the migration of mononuclear cells.

Material and Methods

Chemotaxis of blood mononuclear cells was investigated using the QCM™ colorimetric chemotaxis assay (Millipore, Temecula, Calif.) according to the manufacturer's instructions. Briefly, PBMCs were isolated from RRMS patients using BD CPT vacutainer and treated with 1, 10 and 25 µM of inventive compounds as described in example 5. After 48 h the cells were washed and transferred ($3\times10^5$ cells in 250 µl medium) to the top inserts of 24-well cell migration plate assembly having a pore size of 3 µm. 300 µl of medium containing chemo-attractants MCP-1 (10 ng/mL) and RANTES (10 ng/mL) was then added to the lower chamber. The cells were then allowed to migrate through the filter towards the chemoattractant for 16 h at 37° C. in a humidified cell culture incubator (Thermo Scientific) with 5% $CO_2$ in air. Thereafter, the cells from the lower chamber, i.e. migrated cells, were detected by incubation with the cell viability stain WST-1 for 1 h followed by quantification by measuring the absorbance at 450 nm using a microplate reader (Tecan, Mannedorf, Switzerland).

Results

Figure 16A:
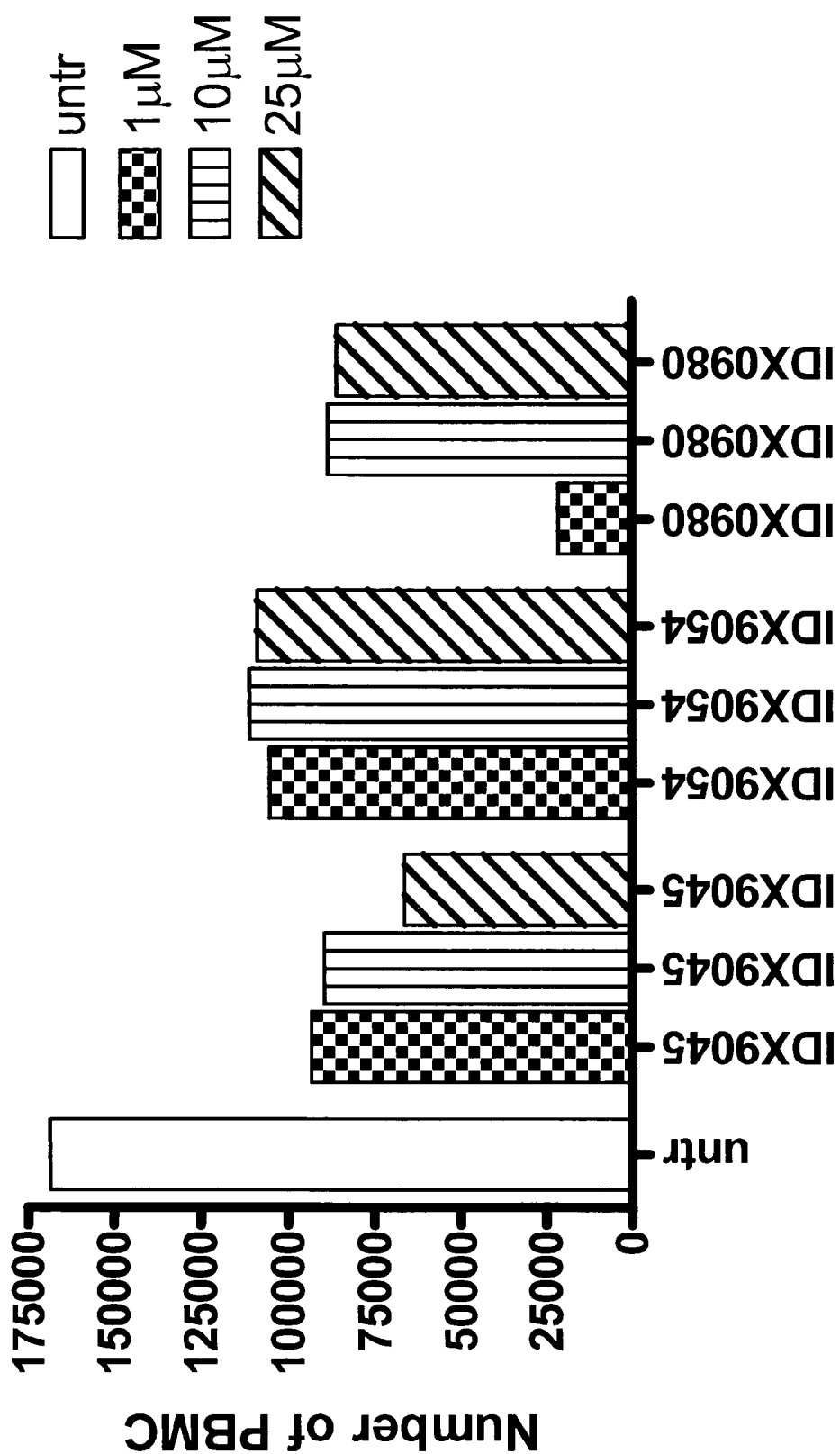
Figure 16B:
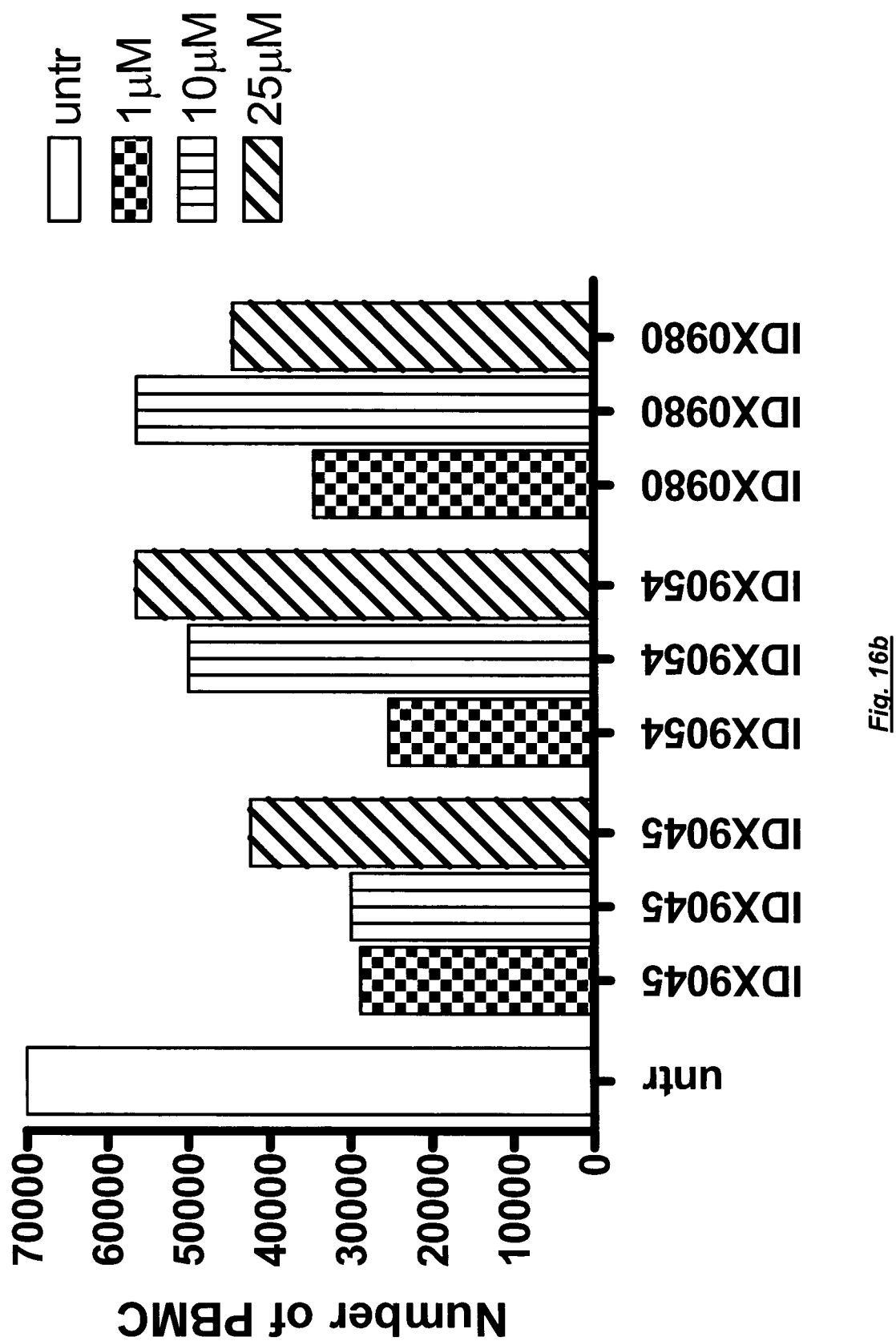

PBMCs isolated from two different RRMS patients treated with inventive compounds (IDX9045, IDX9054, IDX0980) showed less migration than untreated cells towards the chemo-attractants in a functional migration assay (FIG. 16A-B).

This indicates that the reduction of cell migration is due to a lower expression of the receptors. There is reason to predict that these results also reflect an in vivo scenario, consequently leading to less chemotaxis of cells into the central nervous system.

Example 7

Reduction of VEGF In Vitro in Patient Samples

The active lesions in MS are characterized by blood-brain barrier (BBB) breakdown, suggesting that altered vessel permeability is involved in the pathogenesis of the disease. In patients with MS, it has been reported that VEGF induces blood vessel permeability thereby increases the influx of the autoaggressive cells into CNS (Proescholdt M A et al., 2002). To investigate if the inventive compounds can reduce production of VEGF, the inventors used PBMC isolated from RRMS patients for studying production of VEGF upon stimulation with the inventive compounds.

Material and Methods

PBMCs were isolated from RRMS patients (n=6-11) using BD CPT vacutainer. The cells were immediately incubated at 37° C. in a volume of 500 µl of complete RPMI-medium in 48-well plates at a concentration of 2×10$^6$ cells/ml and treated with 1, 10 and 25 µM of each inventive compounds. After 48 h the supernatants were analyzed for presence of VEGF using cytometric bead array (CBA, Becton Dickinson).

Results

PBMC isolated from RRMS patients showed significant VEGF reduction in cell supernatants after stimulation with IDX9038, IDX9045, IDX9004, and IDX0980 (FIG. 17), however, IDX9022, IDX9058, IDX9054, IDX9060, IDX0150 and IDX9052 did not reduce VEGF in the cell supernatant (data not shown).

A reduction of VEGF was observed in the cell supernatant from cells treated with the inventive compounds. This property of the inventive compounds is believed to reduce vascular permeability of the BBB and thereby prevent the infiltration of immune cells into CNS.

Example 8

Induction of IFN-Beta In Vitro in Patient Samples

The inventors used blood from RRMS patients to test different candidate compounds in vitro for induction of IFN-beta.

Material and Methods

PBMCs were isolated from RRMS patients (n=6) using BD CPT vacutainer. The cells were immediately incubated at 37° C. in a volume of 500 µl of complete RPMI-medium in 48-well plates at a conc. of 2×10$^6$ cells/ml and treated with 1, 10 and 25 µM of each of oligonucleotide compounds. After 48 h the supernatants were analyzed for IFN-beta production using an IFN-beta ELISA kit (Invitrogen).

Results

PBMC isolated from RRMS patients showed significant IFN-beta production in cell supernatants after stimulation with IDX9058, IDX9045, IDX9004, IDX9054, IDX9060 and IDX0980 after 48 h (FIG. 18). IDX9022, IDX9038 and IDX 9052 did not induce significant IFN-beta production in supernatant (data not shown). IDX0150 showed no IFN-beta production at all (data not shown).

An increased IFN-beta production was observed in cell supernatant from PBMC isolated from RRMS patients treated with the inventive compounds. This property of the inventive compounds to elicit IFN-beta production could contribute to less inflammation due to the known beneficial effects of this cytokine, as currently used in RRMS therapy.

In general, the results of the experiments performed by the inventors indicate that the oligonucleotides can be effective in an in vivo situation where an inhibition or reduction of mononuclear cells to the central nervous system could be beneficial for the treatment of inflammatory diseases of the CNS. This beneficial effect of the inventive compounds can be mediated through down-regulating the expression of at least one cell surface marker or VEGF.

Although the invention has been described with regard to its preferred embodiments, which constitute the best mode presently known to the inventor, it should be understood that various changes and modifications as would be obvious to one having the ordinary skill in this art may be made without departing from the scope of the invention as set forth in the claims appended hereto.

REFERENCES

FDA News P04-107, Nov. 23, 2004.
Friese, M A et al., The value of animal models for drug development in multiple sclerosis, Brain, 2006; 129 (Pt 8):1940-52.
Gold et al., Understanding pathogenesis and therapy of multiple sclerosis via animal models: 70 years of merits and culprits in experimental autoimmune encephalomyelitis research, Brain, 2006; 129 (Pt 8):1953-71.
Hafler, D A, Multiple sclerosis. J Clin Invest, 2004.
Kerkmann, M. et al., Spontaneous formation of nucleic acid-based nanoparticles is responsible for high interferon-alpha induction by CpG-A in plasmacytoid dendritic cells, J Biol Chem, 2005; 280(9):8086-93.
Wikström, F H et al., Structure-dependent modulation of alpha interferon production by porcine circovirus 2 oligodeoxyribonucleotide and CpG DNAs in porcine peripheral blood mononuclear cells., J Virol. 2007; 81(10):4919-27.
Proescholdt M A. et al, Vascular endothelial growth factor is expressed in multiple sclerosis plaques and can induce inflammatory lesions in experimental allergic encephalomyelitis rats., J Neuropathol Exp Neurol. 2002; 61(10): 914-25
Trebst C, Ransohoff R M. Investigating chemokines and chemokine receptors in patients with multiple sclerosis: opportunities and challenges, Arch Neurol. 2001; 58(12): 1975-80.
Steinman L. A molecular trio in relapse and remission in multiple sclerosis, Nat Rev Immunol., 2009; 9(6):440-7.

The invention claimed is:

1. An isolated and substantially purified oligonucleotide selected from the group consisting of SEQ ID NO: 1 (IDX9045), SEQ ID NO: 2 (IDX9054), SEQ ID NO: 4 (IDX9004), and SEQ ID NO: 8 (IDX9060).

2. The oligonucleotide according to claim 1, wherein at least one nucleotide has a phosphate backbone modification.

3. The oligonucleotide according to claim 2, wherein the phosphate backbone modification is a phosphorothioate or phosphorodithioate modification.

4. A pharmaceutical composition comprising an oligonucleotide according to claim 1.

5. The composition according to claim 4, further comprising a pharmacologically compatible and physiologically acceptable excipient or carrier selected from the group consisting of saline, liposomes, surfactants, mucoadhesive compounds, enzyme inhibitors, bile salts, absorption enhancers, cyclodextrins, or a combination thereof.

6. A pharmaceutical composition comprising an oligonucleotide according to claim 2.

7. The composition according to claim 6, further comprising a pharmacologically compatible and physiologically acceptable excipient or carrier selected from the group consisting of saline, liposomes, surfactants, mucoadhesive compounds, enzyme inhibitors, bile salts, absorption enhancers, cyclodextrins, or a combination thereof.

8. A pharmaceutical composition comprising an oligonucleotide according to claim 3.

9. The composition according to claim 8, further comprising a pharmacologically compatible and physiologically acceptable excipient or carrier selected from the group consisting of saline, liposomes, surfactants, mucoadhesive compounds, enzyme inhibitors, bile salts, absorption enhancers, cyclodextrins, or a combination thereof.

10. A method for the treatment, and/or alleviation of multiple sclerosis, comprising administering an oligonucleotide to a patient in need thereof in an amount effective to inhibit or reduce the influx of mononuclear and/or autoaggressive cells to the central nervous system by down-regulating the expression of at least one specific cell surface marker, wherein the oligonucleotide is an isolated and substantially purified oligonucleotide selected from the group consisting of SEQ ID NO: 1 (IDX9045), SEQ ID NO: 2 (IDX9054), SEQ ID NO: 3 (IDX9038), SEQ ID NO: 7 (IDX9058), SEQ ID NO: 6 (IDX9022), SEQ ID NO: 4 (IDX9004), SEQ ID NO: 8 (IDX9060), and SEQ ID NO: 5 (IDX9052).

11. The method according to claim 10, wherein the oligonucleotide is of SEQ ID NO: 1 (IDX9045).

12. The method according to claim 10, wherein the oligonucleotide is of SEQ ID NO: 2 (IDX9054).

13. The method according to claim 10, wherein the cell surface marker is at least one of CD49d, CXCR3 (CD183), CCR2 (CD192), and CCR5 (CD195).

14. The method of claim 13, wherein the oligonucleotide is selected from the group consisting of SEQ ID NO: 1 (IDX9045), SEQ ID NO: 2 (IDX9054), SEQ ID NO: 7 (IDX9058), and SEQ ID NO: 3 (IDX9038).

15. The method of claim 13, wherein the cell surface marker is CD49d and the oligonucleotide is selected from the group consisting of SEQ ID NO: 3 (IDX9038) and SEQ ID NO: 7 (IDX9058).

16. A method for the treatment, and/or alleviation of multiple sclerosis, wherein an oligonucleotide is administered to a patient in need thereof in an amount effective to inhibit or reduce the influx of mononuclear and/or autoaggressive cells to the central nervous system by reducing the production of VEGF, wherein the oligonucleotide is an isolated and substantially purified oligonucleotide selected from the group consisting of SEQ ID NO: 1 (IDX9045), SEQ ID NO: 2 (IDX9054), SEQ ID NO: 3 (IDX9038), SEQ ID NO: 7 (IDX9058), SEQ ID NO: 6 (IDX9022), SEQ ID NO: 4 (IDX9004), SEQ ID NO: 8 (IDX9060), and SEQ ID NO: 5 (IDX9052).

17. The method of claim 16, wherein the oligonucleotide is selected from the group consisting of SEQ ID NO: 1 (IDX9045) and SEQ ID NO: 2 (IDX9054).

18. The method according to claim 10, wherein the route of administration is chosen from mucosal, subcutaneous, intramuscular, intravenous and intraperitoneal administration.

19. The method according to claim 18, wherein the mucosal administration is chosen from nasal, oral, gastric, ocular, rectal, urogenital and vaginal administration.

20. The method according to claim 16, wherein the route of administration is chosen from mucosal, subcutaneous, intramuscular, intravenous and intraperitoneal administration.

21. The method according to claim 20, wherein the mucosal administration is chosen from nasal, oral, gastric, ocular, rectal, urogenital and vaginal administration.

22. The oligonucleotide according to claim 1, consisting of SEQ ID NO: 1 (IDX9045).

23. The oligonucleotide according to claim 1, consisting of SEQ ID NO: 2 (IDX9054).

24. The composition according to claim 5, wherein the oligonucleotide consists of SEQ ID NO: 1 (IDX9045).

25. The composition according to claim 5, wherein the oligonucleotide consists of SEQ ID NO: 2 (IDX9054).

* * * * *